US011911464B2

(12) United States Patent
Davis et al.

(10) Patent No.: US 11,911,464 B2
(45) Date of Patent: Feb. 27, 2024

(54) ANTI-PARASITIC IMMUNOLOGICAL COMPOSITIONS

(71) Applicants: Prommune, Inc., Topeka, KS (US); Board of Regents of the University of Nebraska, Lincoln, NE (US)

(72) Inventors: Paul Davis, Omaha, NE (US); Samer Al-Murrani, Overland Park, KS (US)

(73) Assignees: Prommune, Inc., Topeka, KS (US); Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 17/275,892

(22) PCT Filed: Sep. 13, 2019

(86) PCT No.: PCT/US2019/050963
§ 371 (c)(1),
(2) Date: Mar. 12, 2021

(87) PCT Pub. No.: WO2020/056229
PCT Pub. Date: Mar. 19, 2020

(65) Prior Publication Data
US 2021/0290761 A1    Sep. 23, 2021

Related U.S. Application Data

(60) Provisional application No. 62/731,353, filed on Sep. 14, 2018.

(51) Int. Cl.
| | | |
|---|---|---|
| *A61K 39/39* | (2006.01) | |
| *A61P 33/02* | (2006.01) | |
| *A61K 39/002* | (2006.01) | |
| *A61K 39/005* | (2006.01) | |
| *A61K 39/008* | (2006.01) | |
| *A61K 39/012* | (2006.01) | |
| *A61K 39/015* | (2006.01) | |
| *A61K 39/018* | (2006.01) | |
| *A61K 39/00* | (2006.01) | |

(52) U.S. Cl.
CPC ............ *A61K 39/39* (2013.01); *A61K 39/002* (2013.01); *A61K 39/005* (2013.01); *A61K 39/008* (2013.01); *A61K 39/012* (2013.01); *A61K 39/015* (2013.01); *A61K 39/018* (2013.01); *A61P 33/02* (2018.01); *A61K 2039/55516* (2013.01); *A61K 2039/6031* (2013.01); *A61K 2039/627* (2013.01)

(58) Field of Classification Search
CPC .... A61K 39/39; A61K 39/002; A61K 39/005; A61K 39/008; A61K 39/012; A61K 39/015; A61K 39/018; A61K 2039/55516; A61K 2039/6031; A61K 2039/627; A61P 33/02

See application file for complete search history.

(56) References Cited

U.S. PATENT DOCUMENTS

| | | |
|---|---|---|
| 7,358,087 B2 | 4/2008 | Sanderson et al. |
| 2008/0280307 A1 | 11/2008 | Gargano et al. |
| 2014/0314839 A1 | 10/2014 | Vetro et al. |
| 2015/0218516 A1 | 8/2015 | Tarantolo et al. |
| 2015/0297668 A1 | 10/2015 | Sanderson |
| 2018/0066018 A1 | 3/2018 | Sanderson et al. |

FOREIGN PATENT DOCUMENTS

| | | |
|---|---|---|
| WO | 1999066043 | 12/1999 |
| WO | 2004007525 | 1/2004 |
| WO | 2002017960 | 12/2004 |
| WO | 2016145365 | 9/2016 |
| WO | 2018/231838 | 12/2018 |

OTHER PUBLICATIONS

Bowie et al (Science, 1990, 257:1306-1310).*
Burgess et al (J. of Cell Bio. 111:2129-2138, 1990).*
Bork (Genome Research, 2000, 10:398-400).*
Ellis (Vaccines, W.B. Saunders Company, Chapter 29, 1988, pp. 568-574).*
Boslego et al (Vaccines and Immunotherapy, 1991, Chapter 17).*
Skolnick et al. (Trends in Biotechnology 18: 34-39, 2000).*
International Search Report and Written Opinion in corresponding PCT/US2019/050963, dated Jan. 22, 2020.
Tan, et al., "Identification of T. gondii epitopes, adjuvants, & host genetic factors that influence protection of mice & humans", Vaccine, 2010, 28(23), pp. 3977-3989.
Cong, et al., "Towards an immunosense vaccine to prevent toxoplasmosis: Protective Toxoplasma gondii epitopes restricted by HLAA*0201", Vaccine, 2011, 29(4), pp. 754-762.
Cong, et al., "Human immunome, bioinformatic analyses using HLA supermotifs and the parasite genome, binding assays, studies of human T cell responses, and immunization of HLA-A*1101 transgenic mice including novel adjuvants provide a foundation for HLA-A03 restricted CD8+T cell epitope based, adjuvanted vaccine protective against Toxoplasma gondii", Immunome Research, 2010, 6(12), 15 pages.
Cong, et al., "Toxoplasma gondii HLA-B*0702 restricted GRA720-28 peptide with adjuvants and an universal helper T cell epitope elicits CD8+ T cells producing IFN-γ and reduces parasite burden in HLAB*0702 mice", Hum Immunol., 2012, 73(1), pp. 1-10.

(Continued)

*Primary Examiner* — Robert A Zeman
(74) *Attorney, Agent, or Firm* — Hovey Williams LLP; Crissa A. Cook

(57) ABSTRACT

Anti-parasitic compounds and uses thereof. Compounds comprising a C-terminal peptide adjuvant conjugated to an N-terminal peptide antigen via a protease-cleavable linker, said peptide adjuvant comprising a peptide analog of C5a, wherein said peptide antigen comprises an antigenic epitope of a parasitic organism, such as *T. gondii*. Methods of therapeutic or prophylactic treatment of a parasitic infections.

11 Claims, 18 Drawing Sheets
Specification includes a Sequence Listing.

(56) References Cited

OTHER PUBLICATIONS

Aklilu, "Veterinary Protozoology—Protozoan Parasites of Veterinary Importance", Universiti Malaysia Kelantan, 2011, 43 pages.
Sahinduran, "Protozoan Diseases in Farm Ruminants", A Bird's-Eye View of Veterinary Medicine, 2012, 23, pp. 473-500.
Sun, et al., "NA vaccination with a gene encoding Toxoplasma gondii GRA6 induces partial protection against toxoplasmosis in BALB/c mice", Parasites & Vectors, Biomed Central Ltd, London UK, 2011, 4(1), p. 213.
Extended Search Report in corresponding European Patent Application Serial No. 19859519.1, dated Aug. 31, 2022.

* cited by examiner

L-cyclohexylalanine (Cha)
YSFKDM(Cha)LaR (SEQ ID NO:1)

ANTI-PARASITIC IMMUNOLOGICAL COMPOSITIONS

CROSS-REFERENCE TO RELATED APPLICATIONS

The present application is the U.S. National Stage of International Patent Application No. PCT/US2019/050963, filed Sep. 13, 2019, which claims the priority benefit of U.S. Provisional Patent Application Ser. No. 62/731,353, filed Sep. 14, 2018, entitled ANTI-PARASITIC IMMUNOLOGICAL COMPOSITIONS, each of which is incorporated by reference in its entirety herein.

FEDERALLY SPONSORED RESEARCH OR DEVELOPMENT

This invention was made with government support under contract #HHSN272201600038C awarded by the National Institutes of Health. The government has certain rights in the invention.

SEQUENCE LISTING

The following application contains a sequence listing in computer readable format (CRF), submitted as a text file in ASCII format entitled "Sequence_Listing_51054-PCT," created on Sep. 12, 2019, as 21 KB. The content of the CRF is hereby incorporated by reference.

BACKGROUND OF THE INVENTION

Field of the Invention

The present invention relates to anti-parasitic compounds comprising a peptide adjuvant conjugated to a parasitic peptide antigen.

Description of Related Art

*Toxoplasma gondii* (*T. gondii*) is an obligate intracellular protozoan parasite capable of infecting all warm-blooded animals, but cats are the only known definitive hosts in which the parasite undergoes sexual reproduction. In some cases of individuals with compromised or immature immune systems, infection causes severe neurological tissue degeneration and birth defects. However, the parasite typically produces no readily observable symptoms in healthy human adults, which may remain in an asymptomatic state of infection (aka latent infection) for life. It is estimated that a third of the world's human population is chronically infected with this parasite. More recently, it has been proposed that even latent *T. gondii* infection is associated with numerous subtle adverse or pathological behavioral alterations in humans and other animals, including rodent models. For example, studies have demonstrated that rodents infected with *T. gondii* have impaired motor performance. More recent personality studies on humans testing positive for *T. gondii* infection indicated that infected men were more likely to disregard rules and were more expedient, suspicious, jealous, and dogmatic.

*T. gondii* infection stimulates production of cytokines IL-2 and IFN-γ by the innate immune system, which ultimately elicits a CD4+ and CD8+ T-cell mediated immune response, thereby preventing subsequent acute infections. Thus, T-cells play a central role in immunity against *Toxoplasma* infection. T-cells recognize *Toxoplasma* antigens that are presented to them by the body's own Major Histocompatibility Complex (MHC) molecules. To evade destruction by the immune system, the parasite ultimately converts to semi-dormant forms called bradyzoites, which cluster together to form tissue cysts. These tissue cysts can form in nearly any tissue, but are predominately deposited and persist in muscle and nervous tissue of the host, especially the brain, eyes, and striated muscle (including the heart).

Consumption of tissue cysts in raw or undercooked meat is one of the primary vectors of *T. gondii* infection, both for humans and other meat-eating, warm-blooded animals. There is currently no human vaccine against *T. gondii* infection. This lack of a vaccine can be traced, in large part, to the lack of vaccine adjuvant capable of generating the necessary immune requirements for effective protection.

SUMMARY OF THE INVENTION

Described herein are anti-parasitic compounds comprising a peptide adjuvant that is a response-selective C5aR agonist conjugated to a peptide antigen of a target parasite. The anti-parasitic compounds initiate cell-mediated immune responses required to protect against *T. gondii* infection, as well as other parasitic infections. The anti-parasitic compounds are taken up by the target cells, the peptide antigen is cleaved, processed, and presented by the cell for immune cell recognition. The anti-parasitic compounds are useful for vaccines against *T. gondii* infection, as well as other parasitic infections. Peptide epitopes/antigens suitable for use in the compounds include those demonstrated immunogenic MHC class I (with additional support for MHC II and/or B cell) epitopes in humans and/or mice. Preferably, such epitopes/antigens comprise an amino acid sequence fully conserved in Type I, II, and III strains of *T. gondii*. More preferably, such epitopes/antigens can be derived from a parasite protein expressed in both the tachyzoite and bradyzoite stages and expressed in high levels (top ⅔ of all measured transcripts).

Thus, embodiments described herein concern anti-parasitic compounds comprising an N-terminal peptide antigen conjugated to a C-terminal peptide adjuvant via a protease-cleavable linker, said peptide adjuvant comprising a peptide analog of C5a (preferably a C5aR agonist), wherein the peptide antigen comprises an antigenic epitope of a parasitic organism. Compositions comprising the such anti-parasitic compounds dispersed in a pharmaceutically acceptable carrier are also described herein.

Embodiments of the invention also concern methods for therapeutic or prophylactic treatment of or induction of an immune response against a parasitic infection. The methods comprise administering anti-parasitic compound(s) according to various embodiments described herein to a subject in need thereof. The disclosure also concerns the use of anti-parasitic compound(s) according to various embodiments described herein to prepare a therapeutic or prophylactic medicament for inducing an immune response against parasitic infection in a subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
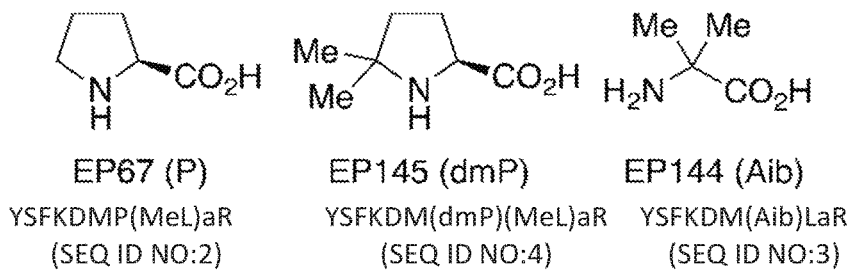
FIG. 1 shows the structure of residue substitutions options for residue 7 in SEQ ID NO:1, with name designations for preferred peptides.
Figure 2:
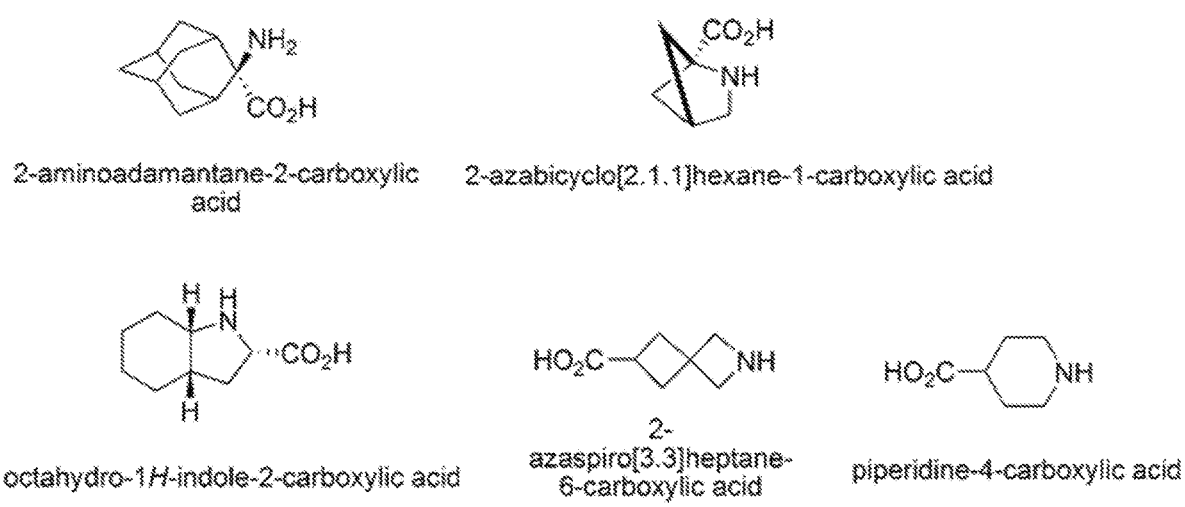
FIG. 2 shows additional residue substitutions for peptide analogs.
Figure 2:
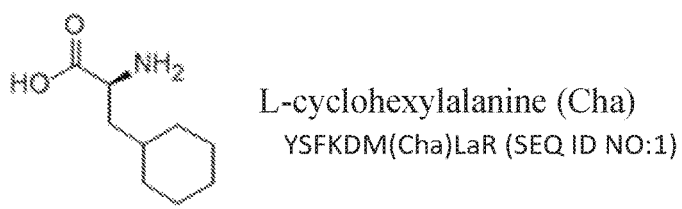
Figure 3:
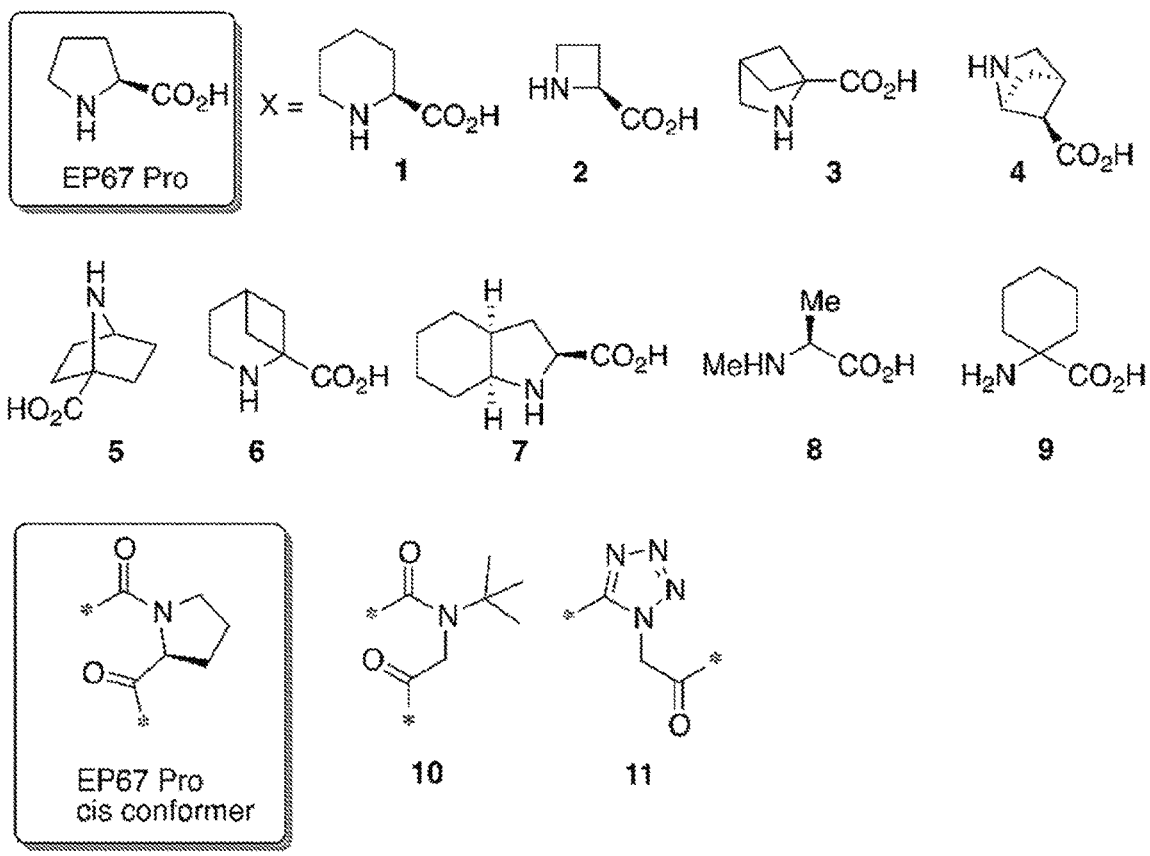
FIG. 3 shows EP67 (proline substitution at position 7) and additional alternative residue substitutions.

The present invention is concerned with anti-parasitic compounds and methods for use in therapeutic or prophylactic treatment of parasitic infections, and specifically oligopeptide products capable of eliciting an immune response to a parasitic infection through selective activation of C5a receptor-bearing antigen presenting cells (e.g., macrophages, monocytes, dendritic cells, etc.) in the absence of triggering harmful inflammatory responses. The anti-parasitic compounds comprise C5aR agonist peptides that selectively bind C5a receptor-bearing antigen presenting cells without binding inflammatory granulocytes, to deliver antigenic moieties for cell presentation and stimulation of the immune response.

The C5aR agonist peptides described in this invention can be used to selectively induce acquired immune responses when coupled with an immunogenic agent, which can then be targeted directly to antigen presenting cells through the specific binding of the agonist peptides. In one or more embodiments, the C5aR agonist peptides are covalently linked to the immunogenic agent (optionally via a spacer moiety), whereby binding of the peptide to an antigen presenting cell C5a receptor activates the antigen presenting cell, effecting delivery of the immunogenic agent to an antigen presenting pathway of the antigen presenting cell. Thus, these agonists are useful as molecular vaccine adjuvants to enhance the efficacy and immune stimulating properties of parasitic vaccine compositions.

Exemplary immunogenic agents for use in the anti-parasitic compounds are peptide antigens and specific peptide epitopes or other antigenic moieties derived from and conserved in the target parasite while avoiding homology to host protein sequences, such that administration of the anti-parasitic compound will provoke a selective immune response (e.g., CD8+ T-cell reactivity) in the host specific to the parasitic organism. Thus, the peptide antigen can be a human or non-human mammalian MHC class I- or class II-restricted antigenic peptide. In other words, the peptide antigen may be "pre-restricted" and represent the antigenic epitope portion of the peptide. In general, MHC class I restricted peptides are from 7-11 amino acids in length, while MCH class II restricted peptides are 10-14 amino acids in length. Alternatively, the peptide antigen conjugated to the peptide adjuvant may be a longer peptide sequence (e.g., ~20 mer), which is processed by the natural antigenic processing machinery of the cell, and thereafter presented on the antigen presenting cell.

It is generally recognized that the requirement for binding and presentation by MHC-I molecules is one of the most selective events of antigen processing and presentation. In one or more embodiments, preferred antigens will have a binding affinity for MHC-I. It will be appreciated that the selected peptide antigens may be species-specific, and in silico or other methods may be used to predict MHC-I affinity for the peptide epitopes to be synthesized and conjugated to the peptide adjuvants for selective delivery to the antigen presenting cells of a particular host. In one or more embodiments, peptide antigens or epitope fragments may be synthesized that are species-agnostic (i.e., reaction across species).

In one or more embodiments, the peptide antigens are linear peptides of less than 16 amino acid residues, and preferably from about 9 to about 15 residues. Exemplary peptide antigens are described herein. Preferred vaccines are listed below that have been shown to work in animal models, including humanized models, as shown below conjugated to a peptide adjuvant, via a cleavable arginine linker:

| Name | Sequence |
|---|---|
| 1. $SAG1_{242-256}$: | *SFKDILPKLSENPWQ*-RR-YSFKDMP(MeL)aR (SEQ ID NO:25) |
| 2. $GRA1_{172-186}$: | *EEVIDTMKSMQRDEE*-RR-YSFKDMP(MeL)aR (SEQ ID NO:26) |
| 3. $AMA1_{41-55}$: | *CAELCDPSNKPGHLL*-RR-YSFKDMP(MeL)aR (SEQ ID NO:27) |
| 4. $SAG3_{208-222}$ | *KRVTCGYPESGPVNL*-RR-YSFKDMP(MeL)aR (SEQ ID NO:28) |
| 5. $GRA6_{210-224}$: | *DRRPLHPGSVNEFDF*-RR-YSFKDMP(MeL)aR (SEQ ID NO:29) |
| 6. $GRA7_{14-28}$: | *GLVAAALPQFATAAT*-RR-YSFKDMP(MeL)aR (SEQ ID NO:30) |

Peptide adjuvants according to the invention are analogs of C5a, and particularly the C-terminal domain of C5a, and are designed to selectively bind C5aR-bearing macrophages (and other APCs) but not C5aR-bearing neutrophils. In particularly preferred embodiments, the present invention is particularly concerned with hydrochloride (HCl) salt forms of these peptide adjuvants, described in detail in co-pending WO 2018/231838, filed Jun. 12, 2018, incorporated by reference in its entirety herein. These peptide adjuvants are linear peptides comprising less than 40 amino acid residues, preferably from 5 to 40 residues, more preferably from 5 to 20 residues, and even more preferably from 5 to 10 residues in length. In one or more embodiments, the peptide adjuvant is a decapeptide (i.e., 10 amino acids in length). A preferred peptide adjuvant that is exemplified in the examples is designated as EP67. This peptide is described in detail in U.S. 2014/0314839, filed Nov. 30, 2012 and U.S. 2015/0297668, filed Jun. 29, 2011, incorporated by reference herein. The recently developed, biologically-compatible HCl salt form of the bioactive peptide EP67 displays enhanced efficacy and quicker acquisition to maximum potency than the trifluoroacetate (TFA) and acetate salt forms. HCl salt forms of conformationally-stable analogs of EP67 are also contemplated herein. "Conformationally-stable" means that the peptide is generally fixed in a single geometric orientation/conformation/molecular arrangement and not prone to conversion/rotation to a different orientation. In other words, rotation of bonds (particularly between the cis and trans configurations) is restricted or eliminated in the conformationally-stable analogs. Individual residue may also have a "constrained conformation," which means that they do not undergo cis/trans isomerization. These conformationally-stable versions of the peptide adjuvant comprise, consist essentially, or consist of the formula:

Tyr-Ser-Phe-Lys-Asp-Met-Xaa-(Xaa2)-(D-Ala)-Arg (SEQ ID NO:1), or HCl salt form thereof, wherein Xaa is a modified proline residue or a residue substitution for proline, and Xaa2 is leucine or N-methyl leucine. The modified proline residue, when used, is one that lacks the cis/trans isomerization of unmodified proline. Advantageously, these peptides have a fixed conformation and selective C5a receptor binding activity. Such conformationally-stable analogs of EP67 are described in detail in co-pending WO 2016/0145365, filed Mar. 11, 2016, and the details of such analogs are incorporated by reference herein in their entirety. Unlike the naturally flexible C5a structure, these peptide analogs are modified to be constrained in a rigid (specific) conformation, contributing to their specificity for C5aR-bearing APCs. Moreover, because cis/trans isomerization is avoided, the peptides are even more constrained in terms of their 3-dimensional binding structure than EP67.

According to one or more embodiments of the invention, exemplary peptide adjuvants include EP67 (where Xaa is P and Xaa2 is MeL, SEQ ID NO:2), EP144 (where Xaa is 2-aminoisobutyric acid and Xaa2 is L, SEQ ID NO:3), or EP145 (where Xaa is 5,5'-dimethylproline and Xaa2 is MeL, SEQ ID NO:4), which are depicted in FIG. 1. Other possible residue substitutions for the proline residue in EP7 are shown in FIG. 2, including 2-aminoadamantane-2-carboxylic acid, 2-azabicyclo[2.1.1]hexane-1-carboxylic acid, octahydro-1H-indole-2-carboxylic acid, 2-azaspiro[3.3]hepane-6-carboxylic acid, piperidine-4-carboxylic acid, and L-cyclohexylalanine (YSFKDM(Cha)LaR (SEQ ID NO:1, where Xaa is cyclohexylalanine and Xaa2 is leucine). Further residue substitutions for the proline residue in EP67 are shown in FIG. 3, including pipecolic acid, 2-azetidinecarboxylic acid, among others shown.

In one or more embodiments, exemplary replacement residues for the proline residue of EP67 (Xaa) include alanine; leucine; isoleucine; N-methylalanine; 2-aminoisobutyric acid; 3-aminoisobutyric acid; N-methylisoleucine; singly-substituted proline analogs at the 2, 3, 4, and/or 5 positions of the pyrrolidine side chain; doubly-substituted proline analogs at the 2, 3, 4, and/or 5 positions of the pyrrolidine side chain; pseudoproline analogs: cysteine-derived thiazolidine, serine-derived oxazolidine, or threonine-derived oxazolidine; trifluoromethylated pseudoprolines; proline analog or homolog having a constrained conformation; trifluoromethylated azetidine 2-carboxylic acid; trifluoromethylated homoserine; oxetanyl-containing peptidomimetic; N-aminoimidazolidin-2-one analog; and nonchiral pipecolic acid analogs. Exemplary singly- or doubly-substituted substituted proline analogs include 5,5'-dimethylproline, 2,4-methano-β-proline, or 2,5-ethano-β-proline. Exemplary serine/threonine/cysteine-derived pseudoproline analogs are selected from the group consisting of:

where R and R'=H or CH₃. Exemplary nonchiral pipecolic acid analogs are selected from the group consisting of:

Exemplary N-aminoimidazolidin-2-one analogs are selected from the group consisting of N-amino-imidazolidinone, α-amino-γ-lactam, and an azapeptide.

Additional C-terminal analogs of C5a are also contemplated herein for use as the peptide adjuvant in the antiparasitic compound, including those comprising, consisting essentially, or consisting of the formula:

A1-Ser-Phe-Lys-A2-A3-A4-A5-A6-A7 (SEQ ID NO:5)

wherein: A1 is Tyr, Trp, or N-acetyl derivatives of Tyr or Trp; A2 is Asp, Gly, Pro or N-methyl derivatives of Asp or Gly; A3 is Ala, Cys, Leu, Met or N-methyl derivatives of Ala, Cys, Leu or Met; A4 is Gln, Leu, Pro or N-methyl derivatives of Gln or Leu; A5 is Pro, Leu, α-methyl Leu or N-methyl Leu; A6 is D-Ala, Gly, D-Pro, aminoisobutyric acid (Aib) or N-methyl derivatives of D-Ala or Gly; and A7 is Arg or N-methyl Arg; such as peptides selected from the group consisting of:

Tyr-Ser-Phe-Lys-Pro-Met-Pro-Leu-(D-Ala)-Arg (SEQ ID NO:6);

Tyr-Ser-Phe-Lys-Asp-Ala-Pro-Leu-(D-Ala)-Arg (SEQ ID NO:7);

Tyr-Ser-Phe-Lys-Asp-Met-Pro-Leu-(D-Ala)-Arg (SEQ ID NO:8);

Tyr-Ser-Phe-Lys-Asp-Met-Pro-Leu-Gly-Arg (SEQ ID NO:9);

Tyr-Ser-Phe-Lys-Asp-Ala-Pro-Leu-Gly-Arg (SEQ ID NO:10);

Tyr-Ser-Phe-Lys-Asp-Cys-Pro-Leu-Gly-Arg (SEQ ID NO:11);

Tyr-Ser-Phe-Lys-Asp-Met-Pro-Leu-(D-Pro)-Arg (SEQ ID NO:12);

Tyr-Ser-Phe-Lys-Asp-Met-Gln-Leu-(D-Ala)-Arg (SEQ ID NO:13);

Tyr-Ser-Phe-Lys-Asp-Met-Gln-Leu-Gly-Arg (SEQ ID NO:14);

Tyr-Ser-Phe-Lys-Asp-Met-Gln-Pro-Gly-Arg (SEQ ID NO:15);

Tyr-Ser-Phe-Lys-Asp-Met-Pro-Leu-Aib-Arg (SEQ ID NO:16);

Tyr-Ser-Phe-Lys-Gly-Met-Pro-Leu-Gly-Arg (SEQ ID NO:17); and

Tyr-Ser-Phe-Lys-Gly-Leu-Leu-Leu-Gly-Arg (SEQ ID NO:18).

In one or more embodiments, the anti-parasitic compound comprises (consists essentially or even consists of) the peptide antigen (or HCl salt thereof) physically linked or conjugated to the peptide adjuvant, and more preferably conjugated to the amino-terminal end of the peptide adjuvant. In one or more embodiments, the peptide antigen is linked to the peptide adjuvant by a cleavable linker, such as a protease-sensitive dipeptide or oligopeptide. In one or more embodiments, the cleavable linker is sensitive to cleavage by a protease of the trypsin family of proteases. In one or more embodiments, the cleavable linker comprises a dibasic dipeptide sequence, such as an Arg-Arg dipeptide sequence or a tetrapeptide Arg-Val-Arg-Arg (SEQ ID NO:78), and the like. Various cleavable linkers can be synthesized by those skilled in the art. The components of the anti-parasitic compound can be made separately, then conjugated, or can be synthesized in tandem by peptide synthetic chemistry according to known methods.

Compositions comprising the anti-parasitic compound are also described herein. The compositions may comprise a single type of anti-parasitic compound (monovalent), or may include a cocktail or mixture of more than one anti-parasitic compound according to the embodiments of the invention (multivalent). For example, the composition could comprise two or more different peptide antigens, three or more different peptide antigens, four or more different peptide antigens, five or more different peptide antigens, even six or more different peptide antigens mixed together and administered as part of the same unit dosage form. In various embodiments, the composition comprises a pharmaceutically acceptable carrier. The term carrier is used herein to refer to diluents, excipients, vehicles, coatings and the like, in which the peptide(s) may be dispersed or coated with for administration. Suitable carriers will be pharmaceutically acceptable. As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained. A pharmaceutically-acceptable carrier would naturally be selected to minimize any degradation of the compound or other agents and to minimize any adverse side effects in the subject, as would be well known to one of skill in the art. Pharmaceutically-acceptable ingredients include those acceptable for veterinary use as well as human pharmaceutical use, and will depend on the route of administration. Any carrier compatible with the excipient(s) and the anti-parasitic compound can be used. Supplementary active compounds may also be incorporated into the compositions.

A composition of the present disclosure is formulated to be compatible with its intended route of administration. Examples of routes of administration include oral administration (ingestion) and parenteral administration, e.g., intravenous, intradermal, subcutaneous, intraperitoneally, inhalation, nasal, transdermal (topical), transmucosal, buccal, sublingual, pulmonary and rectal administration.

Pharmaceutical compositions suitable for injectable use include sterile aqueous solutions (where water-soluble), solutions in sterile isotonic aqueous buffer, or dispersions and sterile powders for the extemporaneous preparation of sterile injectable solutions or dispersion. For intravenous administration, suitable carriers include physiological saline, Cremophor EL™ (BASF, Parsippany, N.J.), bacteriostatic/sterile water/distilled autoclaved water (DAW), or phosphate buffered saline (PBS). In all cases, the composition is sterile and fluid to allow syringability. The carrier may be a solvent or dispersion medium containing, for example, water, ethanol, polyol (for example, glycerol, propylene glycol, and liquid polyethylene glycol, and the like), and suitable mixtures thereof. Fluidity is maintained, for example, by the use of a coating such as lecithin, by the maintenance of the required particle size in the case of dispersion, and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions may be brought about by including in the composition an agent that delays absorption, for example, aluminum monostearate and gelatin. The injectable preparations may be enclosed in ampules, disposable syringes or multiple dose vials made of glass or plastic.

Solutions or suspensions used for parenteral application (injection or infusion) may include the following components: a sterile diluent such as water for injection, saline solution, fixed oils, polyethylene glycols, glycerin, propylene glycol, various oil-in-water or water-in-oil emulsions, as well as dimethyl sulfoxide (DMSO), or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH may be adjusted with acids or bases, such as hydrochloric acid or sodium hydroxide.

Oral compositions generally include an inert diluent or an edible carrier. Oral formulations generally take the form of a pill, tablet, capsule (e.g., soft gel capsule, solid-filled capsule, or liquid-filled capsule), solid lozenge, liquid-filled lozenge, mouth and/or throat drops or spray, effervescent tablets, orally disintegrating tablet, suspension, emulsion, syrup, elixir, or tincture. The composition may be contained in enteric forms to survive the stomach or further coated or mixed to be released in a particular region of the gastrointestinal tract by known methods. Solid oral dosage forms are typically swallowed immediately, or slowly dissolved in the mouth. Oral compositions may also be prepared using a fluid carrier for use as a mouthwash, wherein the compound in the fluid carrier is applied orally and swished and expectorated or swallowed. Oral formulations optionally contain any of the following ingredients, or compounds of a similar nature: a binder such as microcrystalline cellulose, gum tragacanth or gelatin; starch or lactose; a disintegrating agent such as alginic acid, Primogel™, or corn starch; a lubricant such as magnesium stearate; a glidant such as colloidal silicon dioxide; and/or a sweetening agent such as sucrose or saccharin.

For administration by inhalation, the composition is optionally delivered in the form of a spray. The spray may be an aerosol spray from a pressured container or dispenser, which contains a suitable propellant, e.g., a gas such as carbon dioxide, or a nebulizer. The composition is optionally formulated for delivery via a dry powder inhaler (DPI), a metered dose inhaler (pMDI), nasal spray, or a vaporizer. For routes of administration involving absorption of an agent and/or excipient through mucosal membrane, the composition further optionally comprises a penetrant.

Optionally, the composition is formulated as a "liquid respiratory composition," i.e., a composition in a form that is deliverable to a mammal via the oral cavity, mouth, throat, nasal passage or combinations thereof. These compositions can be delivered by a delivery device selected from droppers, pump, sprayers, liquid dropper, spoon, cup, squeezable sachets, power shots, and other packaging and equipment, and combinations thereof. In one embodiment, the liquid respiratory composition comprises the therapeutic agent, and excipient, a thickening polymer (e.g., xanthan gum, cellulosic polymers such as carboxymethylcellulose (CMC), hydroxethylcellulose, hydroxymethylcellulose, and hydroxypropylmethylcellulose, carrageenan, polyacrylic acid, cross-linked polyacrylic acid such as Carbopol®, polycarbophil, alginate, clay, and combinations thereof), and optionally a mucoadhesive polymer (e.g., polyvinylpyrrolidone (Povidone), methyl vinyl ether copolymer of maleic anhydride (Gantrez®), guar gum, gum tragacanth, polydextrose, cationic polymers, poly(ethylene oxide), poly(ethylene glycol), poly(vinyl alcohol), poly(acrylic acid), cross-linked polyacrylic acid such as Carbopol®, polycarbophil, poly(hydroxyl ethyl methacrylate), chitosan, cellulosic polymers such as carboxymethycellulose (CMC), hydroxethylcellulose, hydroxymethylcellulose, and hydroxypropylmethylcellulose, and combinations thereof). The composition is preferably a non-Newtonian liquid that exhibits zero shear viscosity from about 100 centiPoise (cP) to about 1,000,000 cP, from about 100 cP to about 500,000 cP, from about 100 cP to about 100,000 cP, from about 100 cP to about 50,000 cP, from about 200 cP to about 20,000 cP, from about 1,000 to about 10,000 cP at a temperature of about 37° C., as measured according to the Shear Viscosity Method. The pH range of the formulation is generally from about 1 to about 7, from about 2 to about 6.5, and from about 4 to about 6.

In general, additional pharmaceutically-acceptable ingredients for use in the compositions include buffering agents, salts, stabilizing agents, diluents, preservatives, antibiotics, isotonic agents, cell media (e.g., MEM, FBS), flavoring agents, and the like. Exemplary isotonic agents include dextrose, lactose, sugar alcohols (e.g., sorbitol, mannitol), and the like. Stabilizing agents include sugars such as sucrose and lactose, amino acids such as glycine or the monosodium salt of glutamic acid and proteins such as albumin or gelatin, and mixtures thereof. Exemplary preservatives include formaldehyde, thimerosal, and the like.

In various embodiments, in addition to the carrier and peptide analogs described herein, a nasal spray formulation may comprise benzalkonium chloride, camphor, chlorhexidine gluconate, citric acid, disodium EDTA, eucalyptol, menthol, purified water, and/or tyloxapol. An exemplary oral composition may comprise FD&C Blue No. 1, gelatin, glycerin, polyethylene glycol, povidone, propylene glycol, purified water, sorbitol special, and/or titanium dioxide in addition to an excipient and acetaminophen, doxylamine succinate, and phenylephrine HCl (or dextromethorphan).

The formulation is provided, in various aspects, in unit dosage form for ease of administration and uniformity of dosage. "Unit dosage form" as used herein refers to physically discrete units suited as unitary dosages for the subject to be treated, each unit containing a predetermined quantity of the anti-parasitic compound calculated to produce the desired therapeutic effect in association with the required pharmaceutical carrier. The specification for the dosage unit forms are dictated by and are directly dependent on the unique characteristics of the excipient(s) and therapeutic agent(s) and the particular biological effect to be achieved.

Safety and efficacy of compositions described herein are determined by standard procedures using in vitro or in vivo technologies, such as the materials and methods described herein and/or known in the art. Administration may be on an as-needed or as-desired basis, for example, once-monthly, once-weekly, or daily, including multiple times daily, for example, at least once daily, from one to about ten times daily, from about two to about four times daily, or about three times daily. A dose of composition optionally comprises about from about 0.001 mg to about 1000 mg active agent, alternatively from about 2.5 mg to about 750 mg active agent, and alternatively from about 5 mg to about 650 mg of the active agent. In one embodiment, a dose of composition according to the present disclosure comprises about from 0.1 mg to about 0.25 mg. In various embodiments, a dose of composition according to the present disclosure comprises 25 µg, 50 µg, 60 µg, 70 µg, 80 µg, 90 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg or 500 µg. In various embodiments, a dose of composition according to the present disclosure comprises between 25 µg to 500 µg, 50 µg to 400 µg, 100 µg to 300 µg, or 200 µg to 250 µg.

The anti-parasitic compounds and associated compositions are used to induce innate and acquired immune responses against parasites while sparing inflammation. The anti-parasitic compound binds specifically to the C5a receptor on the antigen presenting cell. This binding is followed by internalization of the peptide antigen, which is cleaved from the peptide adjuvant once internalized in the cell, and results in presentation of the antigen moiety on the surface of the antigen presenting cell. In one or more embodiments, compositions used according to the invention comprise a plurality of anti-parasitic compounds, and specifically different anti-parasitic compounds, each comprising a different peptide antigen. Such "cocktail" compositions can be useful to deliver multiple different peptide antigens each conjugated to a peptide adjuvant, and initiate a more robust immune response. The same peptide adjuvant can be used in the composition across the different types of peptide antigens. Alternatively, different peptide adjuvants can be used for different types of peptide antigens. The compositions may be formulated with different antigens to target different types of parasites (i.e., broad spectrum or "cocktail"). Alternatively, the composition may be formulated with different antigens that are nonetheless specific to one particular target parasite.

In one or more embodiments, the target parasite is a protozoan, and particularly a pathogenic protozoan that causes infection in humans or animals. Exemplary target parasites are protozoans, including, without limitation, *Entamoeba histolytica, Eimeria* spp. (*bovis, brunetti, maxima, mitis, acervuline, meleagrimits, crandallis, ovinoidalis, bakuensis, arloingi, ninakohlyakimovue, debliecki, leuckarti, intestinalis, zuernii, auburnesis, alabamensis, phocae, alpacae, invitaensis, lamae, macusaniensis, punonensis, couesii, kinsellai, palustris, ojastii, oryzomysi, necatrix, tenella, stiedae*, etc.), *Isospra* spp., *Besnoitia* spp. (*besnoiti, caprae*, etc.), *Babesia* spp. (*bovis, bigemina, berbera, caballi, equi, perroncitoi, tralirmanni, argentina, divergens, microti, major, jakimovi, ovata, molasi, ovis*, etc.), *Balantidium coli, Giardia* spp. (*lamblia/duodenalis, intestinalis*, etc.), *Neospora caninum, Trichomonas vaginalis, Trypanosoma* spp. (*brucei, cruzi, vivax, theileri, congolense, simiae, melophagium, uniforms, equiperdum*, etc.), *Theileria* spp. (*parva, annulata, orientalis, velifera, taurotragi, sergenti, lestoquardi, mutans, hirci, ovis*, etc.), *Leishmania* spp. (*major, tropica, aethiopica, mexicana, amazonensis, venezuelensis, braziliensis, guyanensis, panamensis, peruviana, donovani, infantum/chagasi*, etc.), *Toxoplasma gondii, Plasmodium* spp. (*vivax, falciparum, ovale*, etc.), *Sarcocystis* spp. (*cruzi, hirsuta, hominis, tenella, gigantica, capracanis, hircicanis, moulei*, etc.), *Spironucleus, Histomonas meleagridis, Cryptosporidium* spp. (*parvum, andersoni, felis*, etc.), *Cytauxzoon felis, Cystoisospora belli, Tritrichomonas* spp. (*foetus, blagburni, augusta*, etc.), *Pentatrichomonas hominis*, and the like.

In use, a therapeutically-effective amount of the anti-parasitic compound is administered to a subject in need thereof. Administration of the anti-parasitic compound elicits an immune response in the subject, and more specifically a selective activation of the innate immune response, without direct activation of pro-inflammatory neutrophils and other granulocytes. The immune response will be demonstrated by a lack of observable clinical symptoms, or reduction of clinical symptoms normally displayed by an infected subject, faster recovery times from infection, reduced duration of infection, and the like. In another embodiment, a method of activating an immune cell at a site of infection or disease is provided comprising administering an effective amount of the anti-parasitic compound to a mammal, wherein the anti-parasitic compound has selective C5a receptor binding activity for targeted delivery and uptake of the peptide antigen. It will be appreciated that although the anti-parasitic compound does not directly bind or activate the pro-inflammatory granulocytes, a secondary inflammatory response may be initiated due to the release of chemokines/cytokines by the APCs once activated by the anti-parasitic compound.

A kit comprising the anti-parasitic compound is also disclosed herein. The kit further comprises instructions for administering the anti-parasitic compound to a subject. The anti-parasitic compound can be provided as part of a dosage unit, already dispersed in a pharmaceutically-acceptable carrier, or it can be provided separately from the carrier. The kit can further comprise instructions for preparing the anti-parasitic compound for administration to a subject, including for example, instructions for dispersing the anti-parasitic compound in a suitable carrier.

It will be appreciated that therapeutic and prophylactic methods described herein are applicable to humans as well as any suitable warm-blooded animal, including, without limitation, dogs, cats, and other companion animals, as well as, rodents, primates, horses, cattle, sheep, pigs, etc. The methods can be also applied for clinical research and/or study.

As used in the present disclosure, the term "treating" or "treatment" refers to an intervention performed with the intention of preventing the development or altering the pathology of infection. Accordingly, "treatment" refers to both therapeutic treatment and prophylactic or preventative measures. A therapeutic agent may directly decrease the pathology of infection, or render the infection more susceptible to treatment by other therapeutic agents or, for example, the host's immune system. Improvement after treatment may be manifested as a decrease or elimination of such symptoms. Thus, the compositions are useful in treating a the infection by preventing the development of observable clinical symptoms from infection, and/or reducing the incidence or severity of clinical symptoms and/or effects of the infection, and/or reducing the duration of the infection/symptoms/effects.

As used herein, the phrase "effective amount" or "therapeutically effective amount" is meant to refer to a therapeutic or prophylactic amount of the anti-parasitic compound or its antigenic peptide that would be appropriate for an embodiment of the present disclosure, that will elicit the desired therapeutic or prophylactic effect or response, including alleviating some or all of such symptoms of infection or reducing the predisposition to the infection, when administered in accordance with the desired treatment regimen. One of skill in the art recognizes that an amount may be considered therapeutically "effective" even if the condition is not totally eradicated or prevented, but it or its symptoms and/or effects are improved or alleviated partially in the subject. The therapeutically effective dosage of antiparasitic compound or its antigenic peptide may vary depending on the size and species of the subject, and according to the mode of administration.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

Peptide Antigen Selection

Selection of peptides for inclusion in *Toxoplasma gondii* peptide-based EP67 vaccines. Criteria for selecting antigenic peptides to include in the vaccine with the C5aR agonist peptide (e.g., EP67) include:

Amino acid sequence distinct by at least 2 amino acids from human, mouse, cow, pig, sheep, dog, and cat
Demonstrated immunogenic MHC class I epitope in humans and/or mice
Demonstrated immunogenic MHC class II epitope in humans and/or mice
Demonstrated immunogenic capacity to promote IgM and IgG B cell responses
Peptide/epitope between 9-15 amino acids in length
(Section of) protein shown to possess chronic or acute protective effects in mice vaccine attempts
(Section of) protein shown to elicit T cell efficacy in humans and/or mice
(Section of) protein shown to elicit serum responses in humans and/or mice
Epitope is derived from a parasite protein expressed in tachyzoite and bradyzoite stage
Computer predicted immunogenicity of MHC class I epitope in BALB/c haplotype
Epitope is derived from a parasite protein expressed at the top ⅔rds of abundant transcripts
Epitope is derived from a parasite protein expressed on the surface or during invasion

Example 2

Peptide Chemistry

Peptides were synthesized with the following antigenic sequences for *Toxoplasma gondii*, and conjugated to either EP67 or a scrambled EP67 sequence (as a control).

| Name | Sequence | SEQ ID NO: | |
|---|---|---|---|
| SAG1$_{242-256}$ | SFKDILPKLSENPWQ | 19 | $M_{calc}$ = 1801; $(M + H)^+$ = 1802; $(M + 2H)^{2+}$ = 901; (104 mg) |
| GRA1$_{172-186}$ | EEVIDTMKSMQRDEE | 20 | $M_{calc}$ = 1838; $(M + H)^+$ = 1839; $(M + 2H)^{2+}$ = 920; (26 mg) |
| AMA1$_{41-55}$ | CAELCDPSNKPGHLL | 21 | $M_{calc}$ = 1595; $(M + H)^+$ = 1596; $(M + 2H)^{2+}$ = 799; (53 mg) |
| SAG3$_{208-222}$ | KRVTCGYPESGPVNL | 22 | $M_{calc}$ = 1618; $(M + H)^+$ = 1619; $(M + 2H)^{2+}$ = 810 (46 mg) |
| GRA6$_{210-224}$ | DRRPLHPGSVNEFDF | 23 | $M_{calc}$ = 1784; $(M + H)^+$ = 1785; $(M + 2H)^{2+}$ = 893; (61 mg) |
| GRA7$_{14-28}$ | GLVAAALPQFATAAT | 24 | $M_{calc}$ = 1401; $(M + H)_+$ = 1402; (65 mg) |

25 mg of each of the following full length anti-parasitic compounds were synthesized in the HCl salt form. All amino acids are L-form except the single "a" residue in each peptide, which is D-form. Residue "MeL" designates an N-methyl leucine.

| Name | Sequence | SEQ ID NO: |
|---|---|---|
| EP67 | YSFKDMP(MeL)aR | 2 |
| scrmbEP67 | (MeL)RMYKPaFDS | 77 |
| SAG1-242EP67: | SFKDILPKLSENPWQRRYSFKDMP(MeL)aR | 25 |
| GRA1-172+EP67: | EEVIDTMKSMQRDEERRYSFKDMP(MeL)aR | 26 |
| AMA1-41+EP67: | CAELCDPSNKPGHLLRRYSFKDMP(MeL)aR | 27 |
| SAG3-208+EP67: | KRVTCGYPESGPVNLRRYSFKDMP(MeL)aR | 28 |
| GRA6-210+EP67: | DRRPLHPGSVNEFDFRRYSFKDMP(MeL)aR | 29 |
| GRA7-14+EP67: | GLVAAALPQFATAATRRYSFKDMP(MeL)aR | 30 |
| SAG1-242+scrmbEP67: | SFKDILPKLSENPWQRR(MeL)RMYKPaFDS | 31 |
| GRA1-172+scrmbEP67: | EEVIDTMKSMQRDEERR(MeL)RMYKPaFDS | 32 |
| AMA1-41+scrmbEP67: | CAELCDPSNKPGHLLRR(MeL)RMYKPaFDS | 33 |
| SAG3-208+scrmbEP67: | KRVTCGYPESGPVNLRR(MeL)RMYKPaFDS | 34 |
| GRA6-210+scrmbEP67: | DRRPLHPGSVNEFDFRR(MeL)RMYKPaFDS | 35 |
| GRA7-14+scrmbEP67: | GLVAAALPQFATAATRR(MeL)RMYKPaFDS | 36 |

Additional predicted HLA peptides include: VVFVVFMGV (GRA6; SEQ ID NO:37); FMGVLVNSL (GRA6; SEQ ID NO:38); FLVPFVVFL (GRA3; SEQ ID NO:39); KSFKDILPK (SAG1; SEQ ID NO:40); AMLTAFFLR (GRA6; SEQ ID NO:41); RSFKDLLKK (GRA7; SEQ ID NO:42); LPQFATAAT (GRA7; SEQ ID NO:43); VPFVVFLVA (GRA3; SEQ ID NO:44); HPGSVNEFDF (GRA6; SEQ ID NO:45); STFWPCLLR (SAG2C 13-21; SEQ ID NO:46); AVVSLLRLLK (SPA/GRA5 89-98; SEQ ID NO:47); and SSAYVFSVK (SRS52A 250-258; SEQ ID NO:48).

Other HLA-A*0201 candidates include:

| ANTIGEN | PEPTIDE SEQUENCES | SEQ ID NO: | LOCATION | PREDICTED IC$_{50}$ | PEPTIDE POOL |
|---|---|---|---|---|---|
| BSR4 | LLAVCMSGV | 49 | 21-29 | 34.3 | P1 |
| GRA15 | FNMNFYIIGA | 50 | 211-220 | 28.8 | |
| GRA10 | YLGYCALLPL | 51 | 686-695 | 8.1 | |
| GRA10 | KLMRQYDMMV | 52 | 323-332 | 11.6 | |
| GRA10 | RLQEIIALA | 53 | 189-197 | 27.8 | |
| GRA10 | FLAGSQVPG | 54 | 54-63 | 35.2 | |
| SAG2C | FMIAFISCFA | 55 | 348-357 | 15.6 | P2 |
| SAG2C | FLSLSLLVI | 56 | 38-46 | 34.1 | |
| SAG2C | SLPLSPFTV | 57 | 147-155 | 40.6 | |
| SAG2D | FMIAFISCFA | 58 | 180-189 | 15.6 | |
| SAG2x | FMIVSISLV | 59 | 1:351-359 | 4.5 | |
| SAG2x | VLSSSFMIV | 60 | 1:346-354 | 27.5 | |
| SAG2x | FVIFACNFV | 61 | 1:44-52 | 40.1 | P3 |
| SAG2x | CLPLYLFVI | 62 | 1:38-46 | 42.2 | |
| SAG3 | FLLGLLVHV | 63 | 375-383 | 2.3 | |

-continued

| ANTIGEN | PEPTIDE SEQUENCES | SEQ ID NO: | LOCATION | PREDICTED IC$_{50}$ | PEPTIDE POOL |
|---|---|---|---|---|---|
| SAG3 | FLTDYIPGA | 64 | 136-144 | 2.8 | |
| SAG3 | FLVGCSLTV | 65 | 306-314 | 5 | |
| SRS9 | VSGFVVAS | 66 | 390-397 | 34.8 | |
| SRS9 | KLMAVCIGGI | 67 | 20-29 | 37.9 | P4 |
| SPA | ITMGSLFFV | 68 | 12-20 | 10.7 | |
| SPA | KLADVLPSA | 69 | 236-244 | 12.3 | |
| SPA | FLCDMDIATL | 70 | 208-217 | 14.1 | |
| SPA | VLALIFVGV | 71 | 20-28 | 20.1 | |
| SPA | GLAAAVVAV | 72 | 82-90 | 27.8 | |
| MIC1 | VLLPVLFGV | 73 | 9-17 | 7.3 | P5 |
| MIC4 | YLIGSGFSA | 74 | 540-548 | 11.8 | |
| MIC6 | MMPSGVPMA | 75 | 80-88 | 22.5 | |
| MICA2P | FAAAFFPAV | 76 | 11-19 | 12.5 | |

It will be appreciated that new sequences may need to be derived or codon optimized for each target species of patient to be treated (generally homologous sequences to those described above). It will be generally appreciated that appropriate sequences will be continually sought through the interrogation of the parasite sequences with species specific MHC epitope-identifying tools using different algorithms, as guided by the selection criteria described herein. See also, Tan et al., *Identification of T. gondii epitopes, adjuvants, & host genetic factors that influence protection of mice & humans*, Vaccine. 2010 May 21; 28(23): 3977-3989; Cong et al., *Towards an immunosense vaccine to prevent toxoplasmosis: Protective Toxoplasma gondii epitopes restricted by HLAA*0201*, Vaccine. 2011 Jan. 17; 29(4): 754-762; Cong et al., *Human immunome, bioinformatic analyses using HLA supermotifs* . . . , Immunome Research 2010, 6:12 (open access); and Cong et al., *Toxoplasma gondii HLA-B*0702 restricted GRA720-28 peptide with adjuvants* . . . , Hum Immunol. 2012 January, 73(1): 1-10, each of which is incorporated by reference herein with respect to disclosed epitope sequences.

Example 3

Peptide Synthesis

Six *T. gondii* vaccines were synthesized: Vaccine 1: SAG$_{1242-256}$ (SEQ ID NO: 25); Vaccine 2: GRA1$_{172-186}$ (SEQ ID NO: 26); Vaccine 3: AMA1$_{41-55}$ (SEQ ID NO: 27); Vaccine 4: SAG3$_{208-222}$ (SEQ ID NO: 28); Vaccine 5: GRA6$_{210-224}$ (SEQ ID NO: 29); Vaccine 6: GRA7$_{14-28}$ (SEQ ID NO: 30). The peptides were an unexpected synthetic challenge, but were ultimately synthesized for testing. Vaccines were purified with analytical and preparative HPLC and characterized with electrospray mass spectrometry:
Vaccine 1: $M_{calc}$=3334; $(M+2H)^{2+}$=1673, $(M=3H)^{3+}$=1113;
Vaccine 2: $M_{calc}$=3376; $(M+2H)^{2+}$=1689; $(M+3H)^{3+}$=1126; $(M=4H)^{4+}$=848

Vaccine 3: $M_{calc}$=3131; $(M+2H)^{2+}$=1566, $(M+3H)^{3+}$=1045;
Vaccine 4: $M_{calc}$=3155, $(M+2H)^{2+}$=1578, $(M+3H)^{3+}$=1052, $(M+4H)^{4+}$=789
Vaccine 5: $M_{calc}$=3320; $(M=2H)^{2+}$=1661; $(M+3H)^{3+}$=1107; $(M+4H)^{4+}$=831
Vaccine 6: $MW_{calc}$=2938; $(M+2H)^{2+}$=1469.6; $(M+3H)^{3+}$=980.4

The doubly- and triply-charged fragmentation ions were consistent with and corresponded to the calculated molecular weights.

Inactive vaccines were also constructed, either with scrambled EP67 or the reverse orientation constructs (with EP67 at the N-terminal end, e.g., EP67-RR-epitope), as negative controls using "inactive" constructs that have the same amino acid composition as the "active" EP67-based vaccines. Synthesis, purification, and characterization was carried out of the *T. gondii* epitopes and the biologically inert vaccines; i.e., the reverse orientation constructs (EP67 on the N-terminal side and the epitope on the C-terminal side) and the normal orientation constructs, but with scrambled sequence EP67 on the C-terminal side.

Free EP67 (unattached to any epitope) was used as a control to stimulate murine bone marrow-derived dendritic cells (See Table 1 below). Preliminary data show that EP67 is capable of inducing all four cytokines initially evaluated: IL-10, CXCL1, TNF-alpha, and IL-6. Testing these and additional cytokines (at the gene and protein-expression levels) against all of the synthesized and control vaccines is carried out. Similarly, we will also be analyzing surface marker expression indicative of DC activation.

TABLE 1 qPCR Detection of Cytokine Expression Following Exposure to EP67

| Cytokine | Fold change | +/- |
|---|---|---|
| IL-10 | 4.13 | 0.64 |
| CXCL1 (a.k.a. KC) | 1.61 | 0.63 |

TABLE 1-continued qPCR Detection of Cytokine Expression
Following Exposure to EP67

| Cytokine | Fold change | +/− |
|---|---|---|
| TNF alpha | 2.14 | 0.59 |
| IL-6 | 3.40 | 0.58 |

EP67 (50 µg/ml) was incubated with bone marrow-derived mouse dendritic cells (24 hrs) following in vitro maturation. Fold changes in expression were compared to PBS controls and normalized to Actin B gene expression. Three replicates were analyzed per gene. The results show that EP67, compared to PBS controls, caused increased expression of IL-10, CXCL1, TNF-alpha and IL-6. A positive control, bacterial LPS, was also evaluated and produced upregulation of at least 20-fold above PBS controls for all evaluated cytokines.

Example 4

Cytokine Release Caused by EP67 Analogs

The synthesis of these vaccines has been an unexpected synthetic challenge. While all vaccines have been synthesized using our standard solid-phase methods, HPLC purification has been challenging given the inefficiency of individual coupling reactions, particularly as the peptide increases in length. Against this backdrop, considerable time was spent in implementing an improved method of synthesis to overcome this problem, using a variety of coupling reagents.

Purification/Desalting. An improved method for generating the HCl salt forms of the peptides was developed. Our standard method of HPLC purification used 0.1% TFA as the running buffer and peptides were brought off the C18 column with a gradient of 60% acetonitrile in 0.1% TFA. This method is used by numerous laboratories and has served us well for many years. However, the final peptide is in the trifluoro-acetate salt form, which some have reported to be disruptive in biological systems due to the generation of TFA. Thus, we have interests in generating the FDA-acceptable HCl salt forms of these *T. gondii* vaccines.

In one approach, the HCl salt forms of our peptides were generated by mixing the peptide in a water slurry with the strong anion exchange resin Amberlite IRA-400 Cl for a few hours. While this was effective in removing most of the TFA counter anions, it was not 100% effective (as indicated by $^{19}$F-NMR). Also, the anion exchange resin gave a slight color change to the otherwise white peptide along with a fair amount of micro resin particles that required filtration. Once removed, the peptide in aqueous solution needed to be re-lyophilized to the dry powder. This desalting, filtering, and lyophilizing process was time consuming and added the possibilities of introducing impurities to the final product.

Another approach is an improved single-step method for generating the HCl salt forms of the above vaccines. This was accomplished by first eliminating the use of TFA in our HPLC purification. In place of 0.1% TFA we used 2% trimethylamine/phosphoric acid buffer, which we found to be an excellent buffer system particularly at the high flow rates we use on our preparative column for final purification of the crude peptide. Under these conditions, the phosphate salt of the peptide is generated, but it is easily exchanged with the HCl salt by loading the peptide onto the same preparative column equilibrated with 5 mM HCl and bringing it off with a rapid gradient of acetonitrile. This method of purification and desalting is now our standard operating procedure for all peptides generated in our laboratory.

Figure 4A:
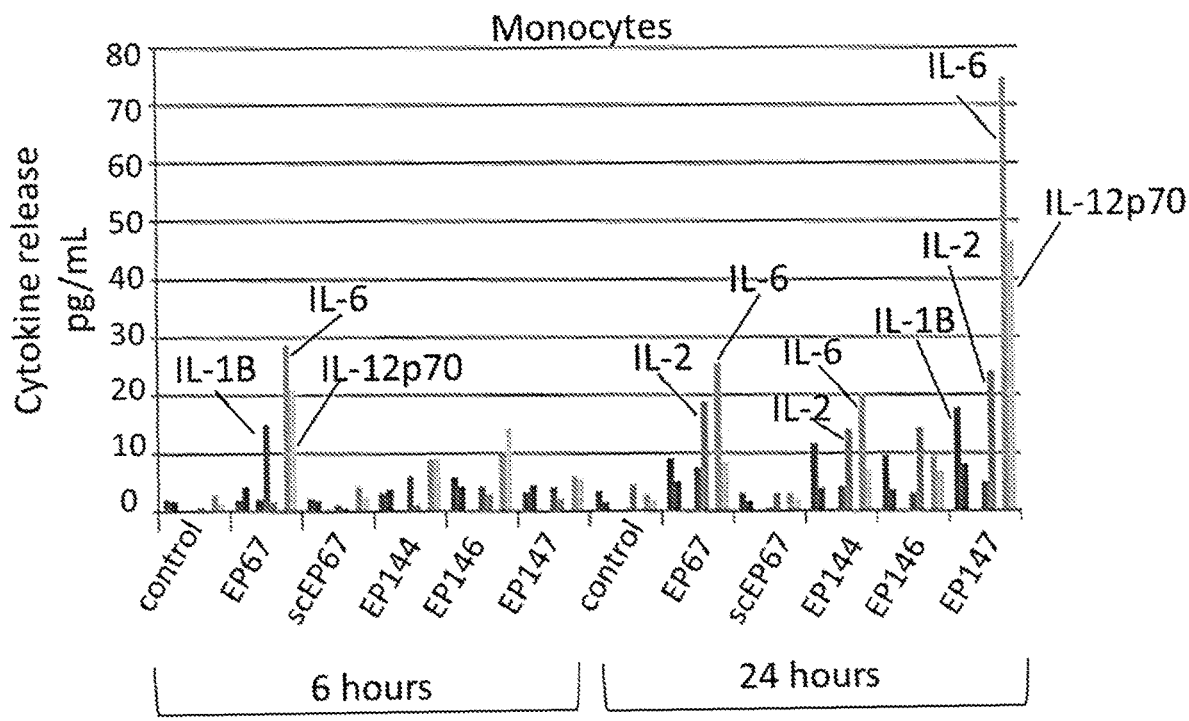
FIG. 4A show the results of exposure of human monocytes to analogs over the course of 6 and 24 hours.
Figure 4B:
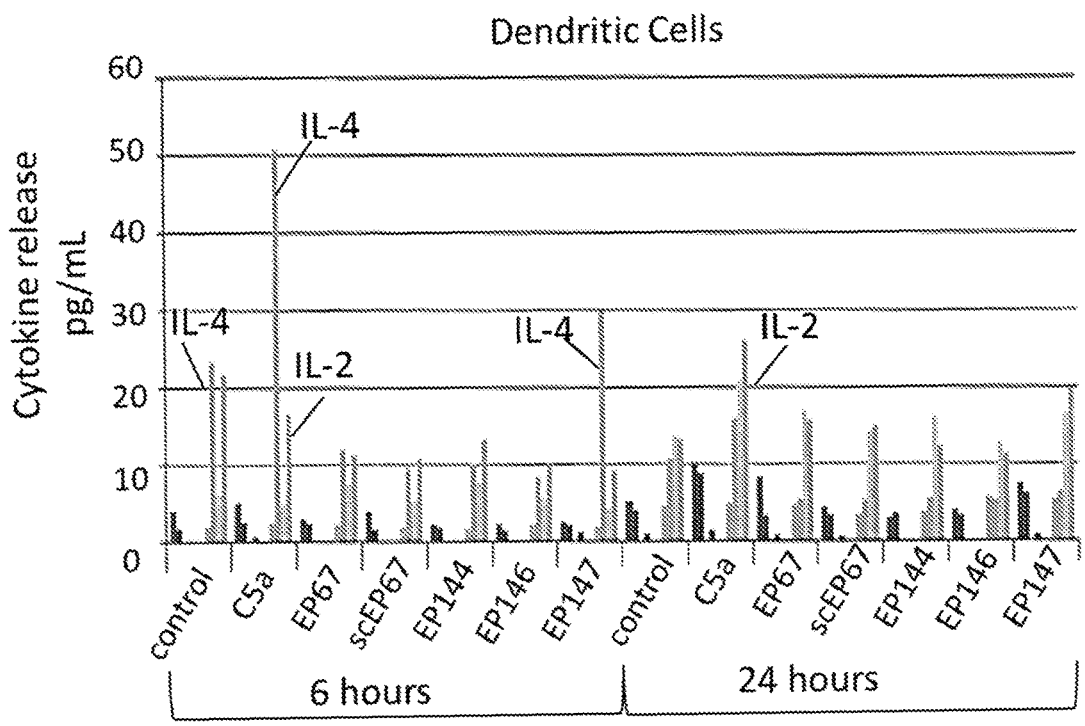
FIG. 4B show the results of exposure of human monocyte-derived dendritic cells to analogs over the course of 6 and 24 hours.

Cytokine Analysis. Considerable time was spent in learning the methods for the rapid, efficient, and high throughput method of cytokine analysis using a multiplex instrument for large panels of cytokines (MesoScale QuickPlex SQ 120). With this instrument, we tested the EP67- and analogue-mediated release of a pro-inflammatory and anti-inflammatory panel of cytokines (IL-1beta, IL-2, IL-4, IL-6, IL-10, IL-12p70, IL-13, IL-15, TNF-α, and IFN-gamma) from human monocytes and monocyte-derived dendritic cells over the course of 6 and 24 hours of exposure 50 µg/ml EP67, scrambled EP67 (scEP67), and EP67 analogues (EP144, EP146, and EP147). These results are shown in FIG. 4. It was encouraging to see cytokine release from EP67-treated cells and interesting to note an increase in cytokine release from the analogue EP147 (cha substitution for proline).

Example 5

Improved Synthesis of Peptides

The analytical HPLC chromatograms of each epitope and EP67-based vaccine were analyzed. In all cases, HPLCs were run on $C_{18}$-bonded silica reverse-phase columns equilibrated with 0.5% trimethylamine (v/v) and 0.5% phosphoric acid (v/v) (TEAP buffer pH 2.3—solvent system A) and peptides eluted with an increasing gradient of 60% acetonitrile in TEAP (solvent system B). Analytical flow rates were 1.5 mL/min and preparative flow rates were 60 mL/min. In both analytical and preparative modes, peptide separations were monitored at 214 nm.

Synthesis of the epitopes was carried out and the crude chromatograms indicated a reasonably clean mixture after resin cleavage and peptide precipitation. Each epitope was purified using preparative HPLC in the manner described above and was generated in the HCl salt form using newly developed methods.

Synthesis of the EP67-based vaccines was more challenging, but our improved synthetic methods gave a significant improvement in yield and purity as indicated by the crude analytical chromatograms after resin cleavage and peptide precipitation. Each EP67-based vaccine was purified using preparative HPLC as described above and generated in the HCl salt form. The exception was vaccine #5 (GRA6$_{210-224}$), which gave two prominent analytical peaks, both of which were collected and analyzed by mass spectrometry. Neither peak, however, gave the calculated molecular weight. The larger of the two peaks generated a molecular weight suggestive of an extra Ser reside during synthesis.

Finally, we began the synthesis of the negative-control "inactive" vaccines; i.e., the same constructs in the above table, but with scrambled sequence EP67 in place of normal sequence EP67. "Inactive" vaccines #1 and #2 have been synthesized.

The crude analytical HPLC chromatograms of each "inactive" vaccine construct were analyzed. As before, HPLCs were run on $C_{18}$-bonded silica reverse-phase columns equilibrated with 0.5% trimethylamine (v/v) and 0.5% phosphoric acid (v/v) (TEAP buffer pH 2.3—solvent system A) and peptides eluted with an increasing gradient of 60% acetonitrile in TEAP (solvent system B). The HCl salt forms of these peptides were generated by loading the peptide collected from the TEAP preparative run onto the same preparative column, but equilibrated with 5 mM HCl and brought off the column with a gradient of acetonitrile (0-50%) of acetonitrile over 5 minutes. Analytical flow rates were 1.5 mL/min and preparative flow rates were 60 mL/min. In both analytical and preparative modes, peptide separations were monitored at 214 nm.

Example 6

Generation and Activation of Human DCs

Figure 5:
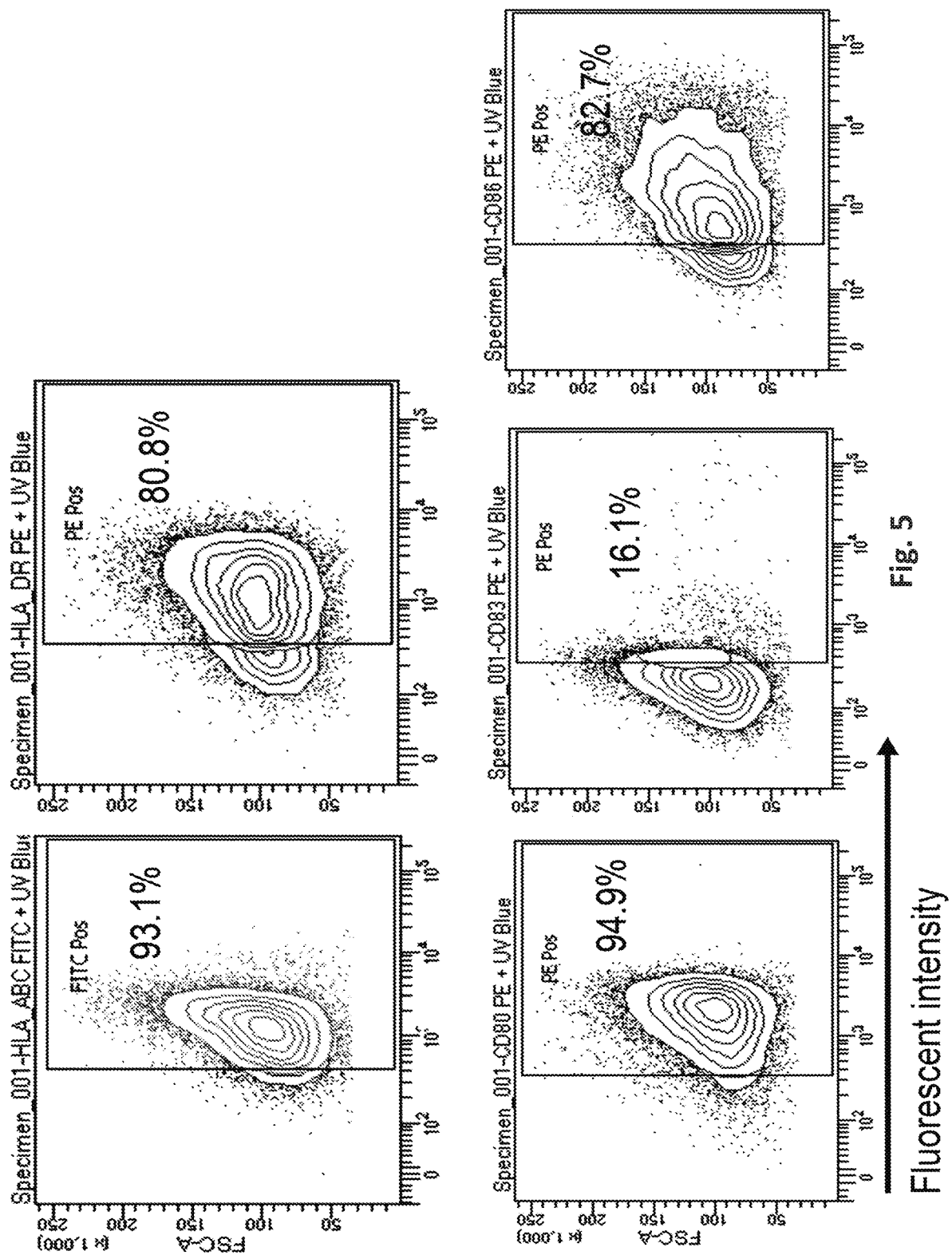
FIG. 5 shows the immunophenotypes of human dendritic cells generated from peripheral blood monocytes as analyzed with flow cytometry.

We established the ability to routinely generate human DCs. FIG. 5 shows the immunophenotypes of human dendritic cells generated from peripheral blood monocytes as analyzed with flow cytometry. Human peripheral blood monocytes (obtained from the elutriation core facility at the University of Nebraska Medical Center) were incubated in the presence of IL-4 (400 U/ml) and GM-CSF (800 U/ml) for 6 days with half of the media replaced at day three. The resulting cells expressed high levels of surface markers CD80, CD83, CD86, HLA-ABC, HLA-DR characteristic of DCs.

Figure 6:
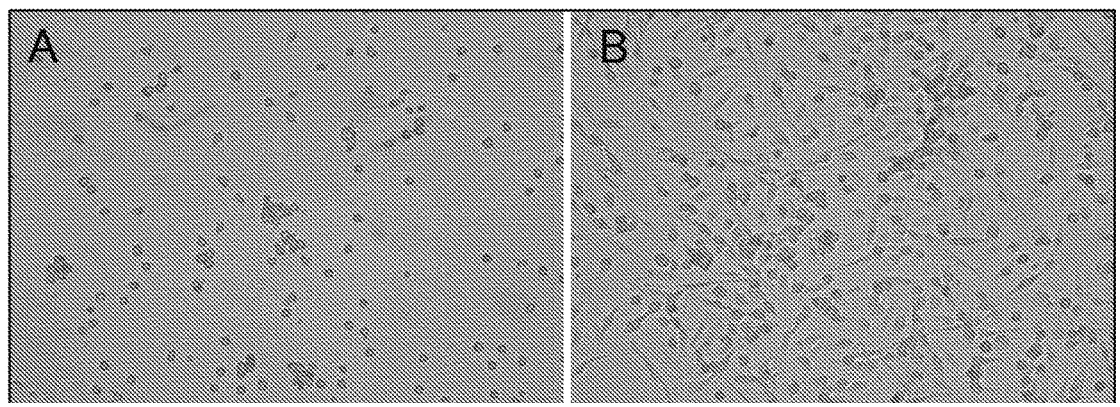
FIG. 6 shows human monocytes (ca. $10^4$) incubated 48 hrs in the presence of 50 µg/ml of scrambled sequence EP67 (Panel A) and EP67 (Panel B). 20× magnification.
Figure 7A:
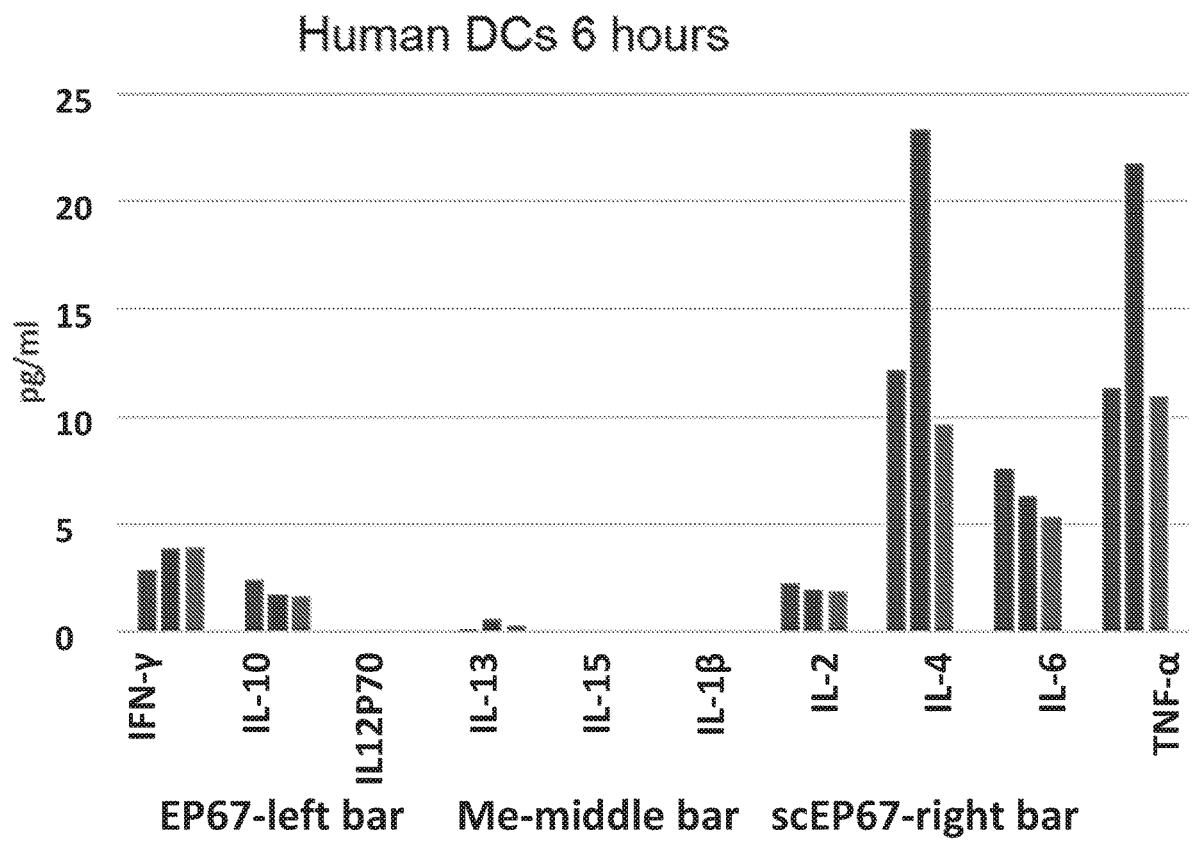
FIG. 7A shows a graph of cytokine release from human DCs incubated for 6 hours with EP67 (50 µg/ml), scrambled (sc) EP67 (50 µg/ml), and media only (Me)
Figure 7B:
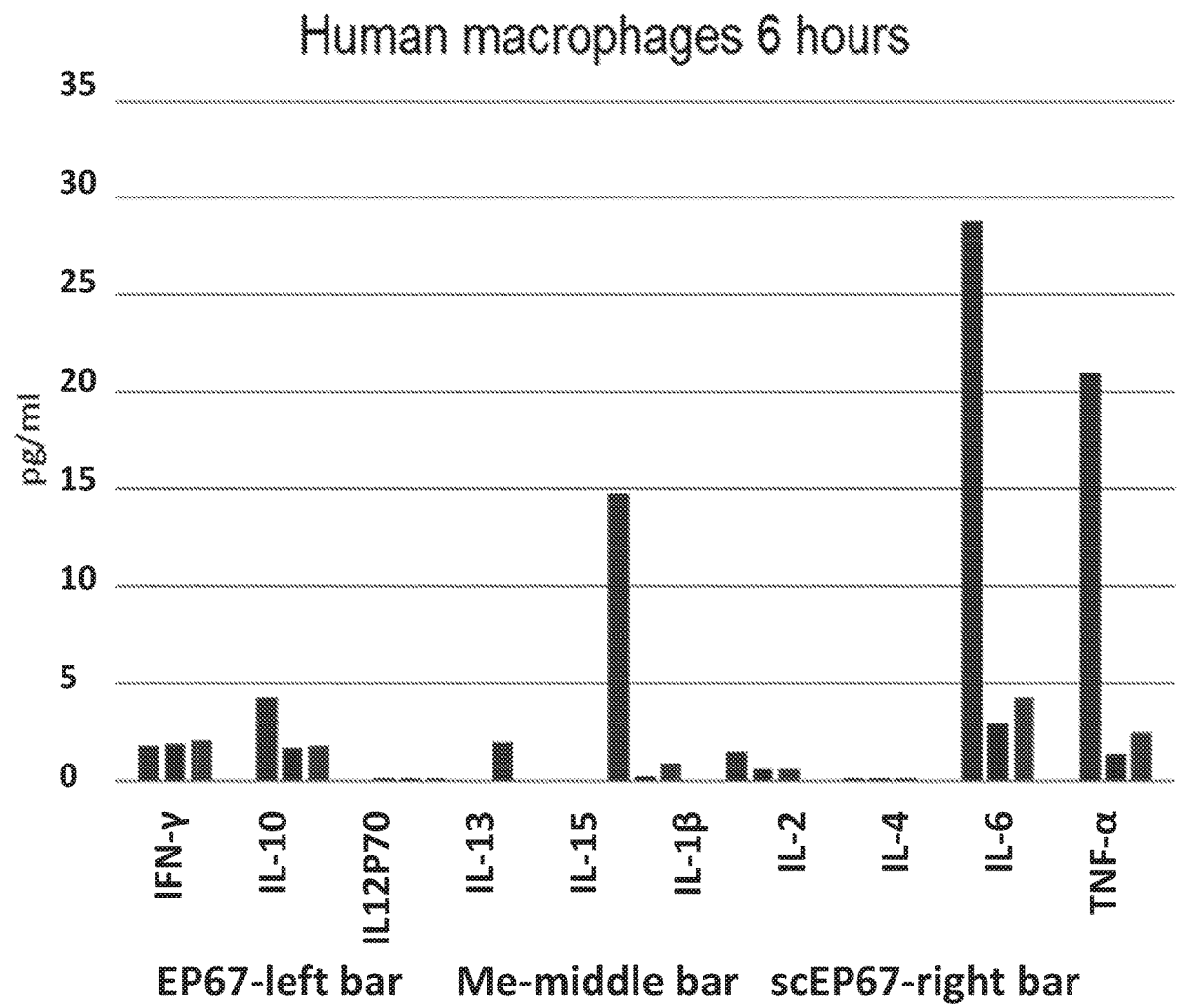
FIG. 7B shows a graph of cytokine release from human macrophages (MC) incubated for 6 hours with EP67 (50 µg/ml), scrambled (sc) EP67 (50 µg/ml), and media only (Me)
Figure 7C:
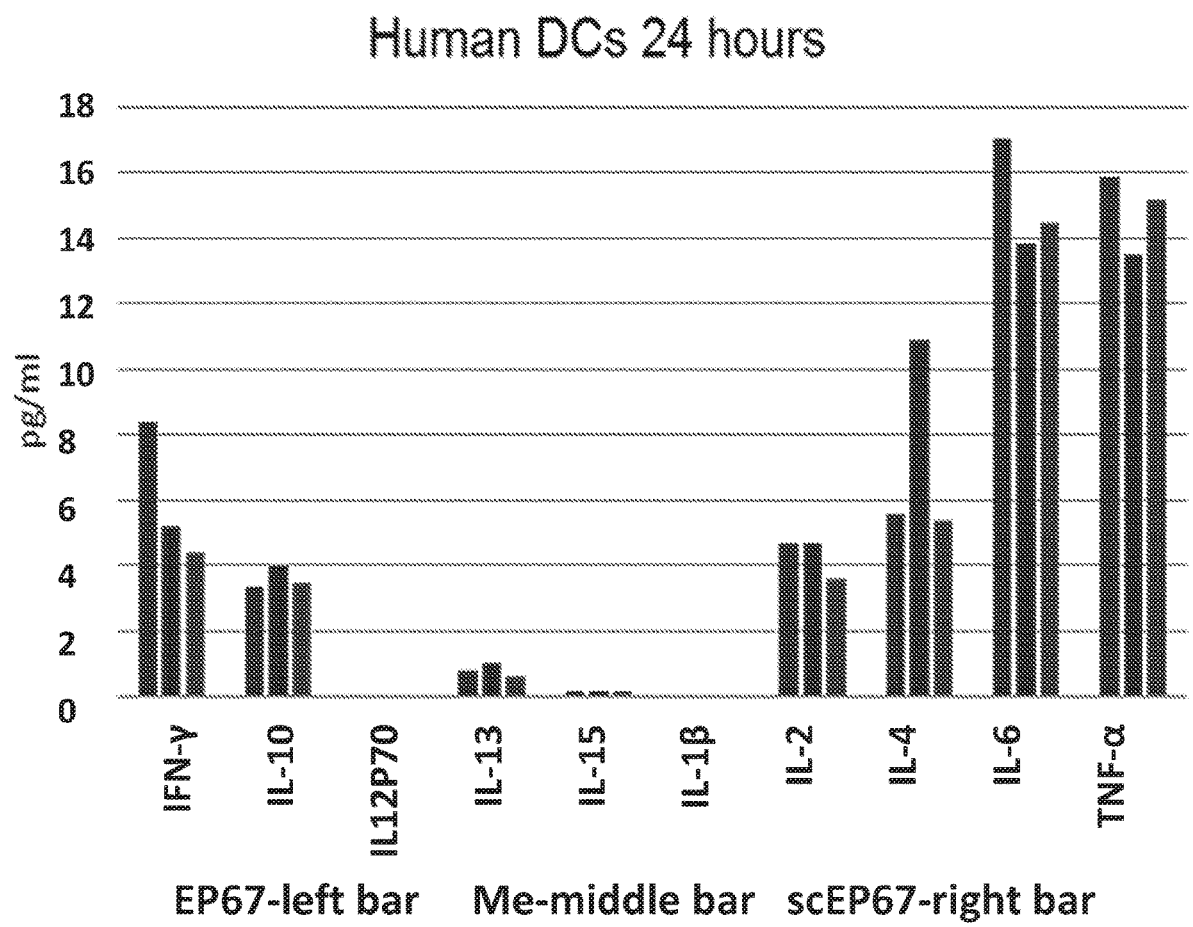
FIG. 7C shows a graph of cytokine release from human DCs incubated for 24 hours with EP67 (50 µg/ml), scrambled (sc) EP67 (50 µg/ml), and media only (Me)
Figure 7D:
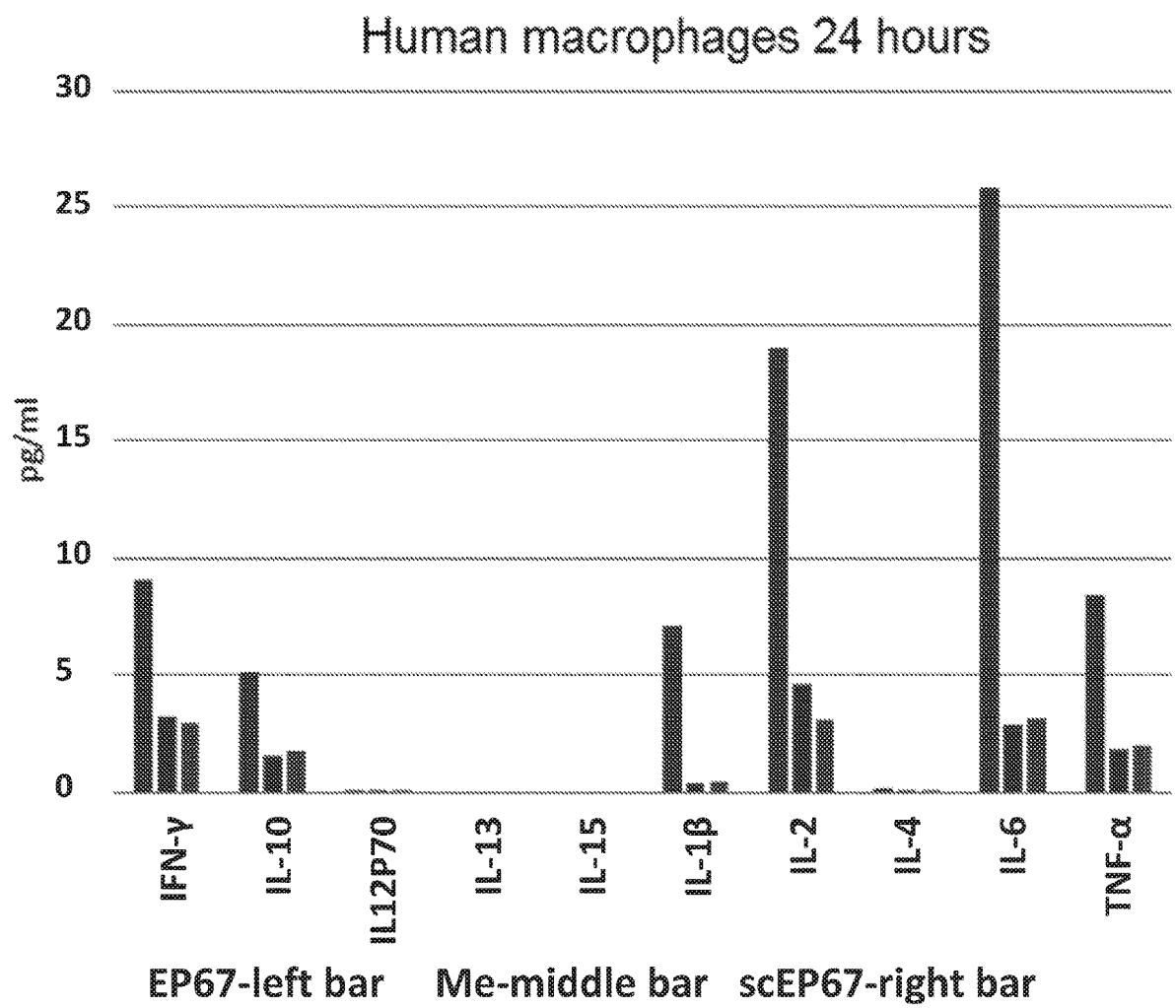
FIG. 7D shows a graph of cytokine release from human macrophages (MC) incubated for 24 hours with EP67 (50 µg/ml), scrambled (sc) EP67 (50 µg/ml), and media only (Me)

EP67 Differentiates Human Peripheral Blood Monocytes to Cells with Phenotypes Characteristic of Macrophages/DCs. EP67, but not scrambled EP67, converts rounded and non-adhered monocytes into elongated, adhered cells that display spindle-like features characteristic of macrophages/DCs. FIG. 6 shows human monocytes (ca. $10^4$) incubated 48 hrs in the presence of 50 µg/ml of scrambled sequence EP67 (Panel A) and EP67 (Panel B).

EP67 Differentiates Human Peripheral Blood Monocytes to Cells with Immunophenotypes Characteristic of Macrophages/DCs. Human monocytes were incubated with EP67 (50 µg/ml) and surface markers analyzed over the course of 7 days. The data shows that EP67 moderately enhanced the expression of CD14, CD16, CD11b, and CD33, but significantly enhanced the expression of CD80 and CD206, which are characteristic of macrophages and DCs.

EP67 Induces Cytokine Release from Human Macrophages and DCs (FIG. 7). Human monocyte-derived macrophages and DCs were incubated with EP67 (50 µg/ml) and scrambled EP67 (50 µg/ml) for 6 and 24 hours. Supernatants were collected and analyzed for the presence of the following cytokines: IL-1beta, IL-2, IL-4, IL-6, IL-10, IL-12p70, IL-13, IL-15, TNF-alpha, and IFN-gamma. FIG. 7 shows graphs of Cytokine release from human DCs and macrophages (MC) incubated for 6 and 24 hours with EP67 (50 µg/ml), scrambled (sc) EP67 (50 µg/ml), and media only (Me). As shown in FIG. 7, EP67 (but not scrambled EP67) induced the release of predominately IL-1beta, IL-2, IL-6, IFN-gamma, and TNF-alpha after 24 hours of incubation with macrophages and DCs. Interestingly, the levels of cytokines induced and the distinction of cytokine release between EP67 and controls was more pronounced in macrophages than in DCs. It is worth noting that the prominent cytokines released at 6 and 24 hours in response to EP67 (IL-1beta, IL-2, IL-6, and TNF-alpha) represent a $T_H1$/pro-inflammatory bias relative to the $T_H2$/anti-inflammatory cytokines (IL-4, IL-5, IL-10, and IL-13). This $T_H1$ bias is in keeping with earlier observations with EP67 and is an important immunologic component for an effective immune response to *T. gondii*.

Figure 8:
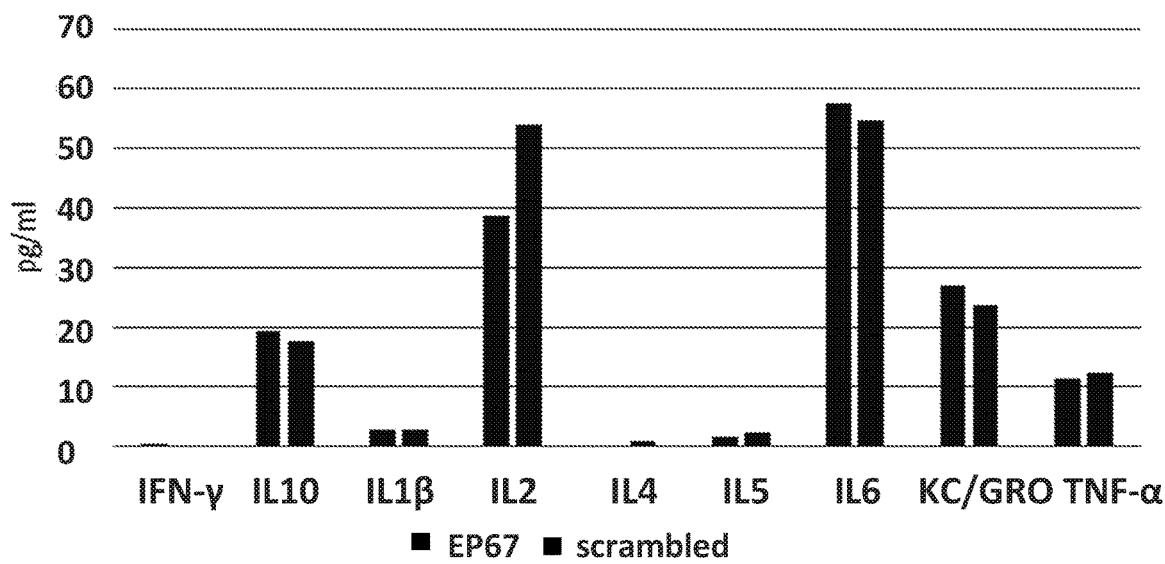
FIG. 8 shows Cytokine release from Balb/c splencoytes (left panel) and splenocytes obtained from aged sentinel mice (right panel) incubated with EP67 and scrambled EP67 (50 µg/ml) for 48 hours.
Figure 8:
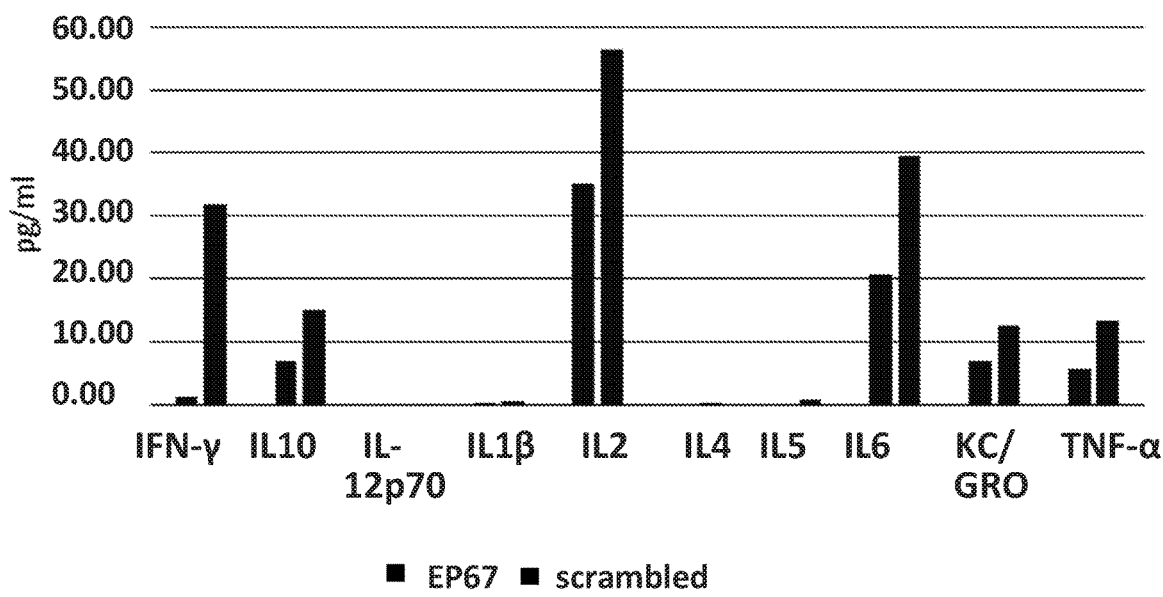

EP67 Induces Cytokine Release from Murine Splenocytes (FIG. 8). Splenocytes were obtained from normal Balb/c mice (ca. 2 months) and aged (ca. 17 months) sentinel mice of undetermined background (a gift from the University of Nebraska Medical Center Animal Facility). Spelocytes were cultured in the presence of EP67 and scrambled EP67 (50 µg/ml) for 24 hours, supernatants harvested, and analyzed for the presence of IL-1beta, IL-2, IL-4, IL-5, IL-6, KC/GRO, IL-10, IL-12p70, TNF-alpha, and IFN-gamma. FIG. 8 shows Cytokine release from Balb/c splencoytes (left panel) and splenocytes obtained from aged sentinel mice (right panel) incubated with EP67 and scrambled EP67 (50 µg/ml) for 48 hours. As shown in FIG. 8, there was little effect of EP67 in cytokine release relative to controls in the Balb/c splenocytes. A more pronounced effect, however, was observed with the aged sentile mice. Splenocytes were not our original choice of APCs from mice to evaluate the effects of EP67/EP67-based vaccines, but they were chosen for this first assessment as a matter of convenience to help with getting our cell culture protocols and assays established and verified.

Summary. We have established the ability to generate human macrophages and DCs and verified their ability to respond to EP67 by upregulation of surface activation markers and cytokine release. These cells will be used for the analogous in vitro assessment of activity of the EP67-based vaccines to *T. gondii* already generated and chemically verified. We also generated murine APCs in form of splenocytes. As mentioned above, these were used as an initial and convenient way to optimize our cell culture conditions and our multiplex cytokine release assays. Our objective moving forward is to establish the ability to generate more "purified" murine APCs (macrophages and DCs) in a manner consistent with what we showed this month with human macrophages/DCs.

Example 7

Activation of Murine DCs by EP67 Vaccines

Figure 9:
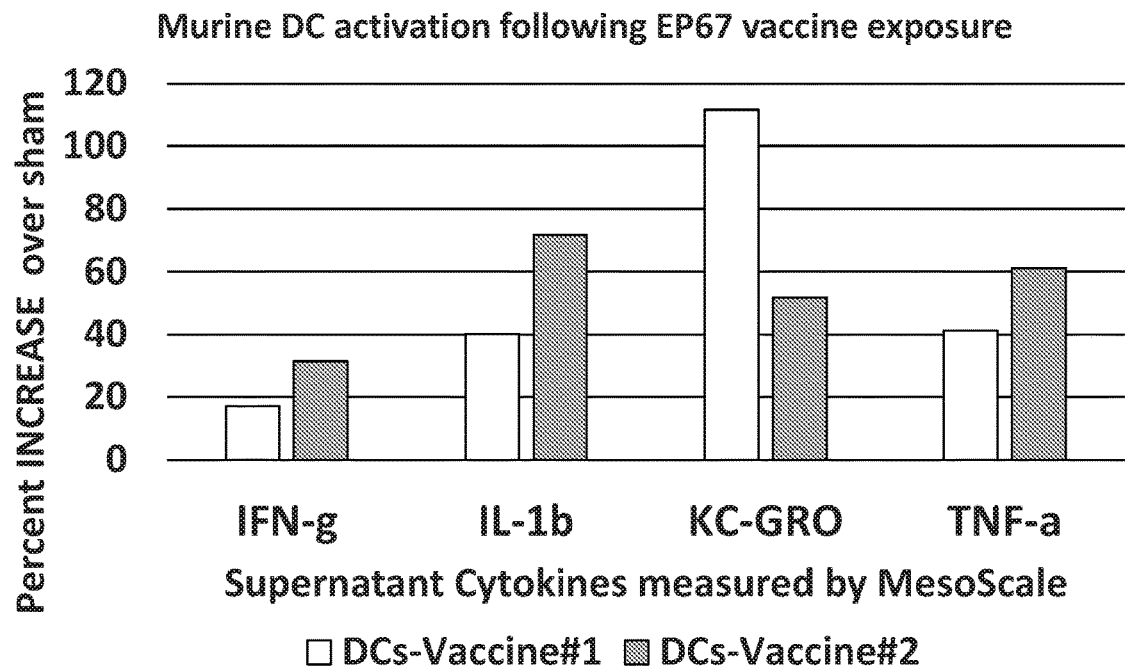
FIG. 9 shows Murine dendritic cell activation following 6 hr exposure to EP67 vaccines.

A subset of vaccines were developed with murine DC's from BALB/c bone marrow, and examined for cytokine response. FIG. 9 shows murine dendritic cell activation following 6 hr exposure to EP67 vaccines. Bone marrow-derived BALB/c DCs were separately exposed to EP67-containing vaccines #1 (TgSAG1) and #2 (TgGRA1) (Example 3), and compared to sham exposure (media). The results were promising for the two vaccines that we tested (FIG. 9) in that exposure led to cytokine release above the controls, but only KC/GRO achieved at least an 80% increase compared to sham (our criteria for active vaccines). KC/GRO, also known as CXCL1, is a potent neutrophil chemotactic cytokine. Increases in INF-gamma, IL-1b, and TNF-α were also observed, and are in-line with expectations of EP67 engagement of the C5a receptor and subsequent activation of dendritic cells.

Example 8

Expression of Leukocyte Surface Markers Indicative of Activation

Figure 10:
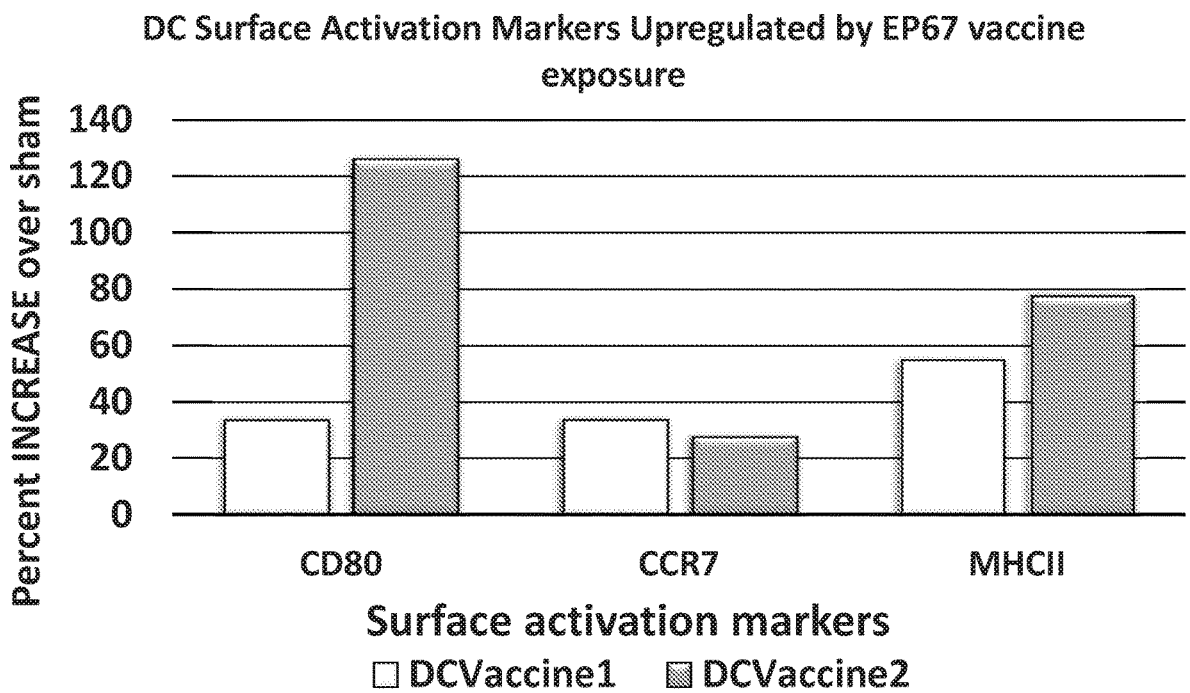
FIG. 10 increase surface activation markers of exposed dendritic cells following exposure to EP67 vaccines.

EP76-containing vaccines were investigated and found to increase surface activation markers of exposed white blood cells, such as DCs shown in FIG. 10, which were exposed for 6 hours to Vaccines #1 (TgSAG1) and #2 (TgGRA1). Following exposure, cells were fixed and stained with antibodies to measure cell surface markers of intact cells by flow cytometry. Increases were observed in key markers of activation, including a sizeable increase (passing the required threshold of 80% increase) in CD80 from EP67 vaccine #2. Elevation occurred in CD80, CCR7, and MHC Class II molecules, indicating activation of dendritic cells compared to control (media only). As noted previously, human in vitro experiments suggest that EP67 containing vaccines more strongly activate macrophages following a six hour exposure.

Example 9

EP67 Vaccines Exhibit No Measurable Toxicity

Figure 11:
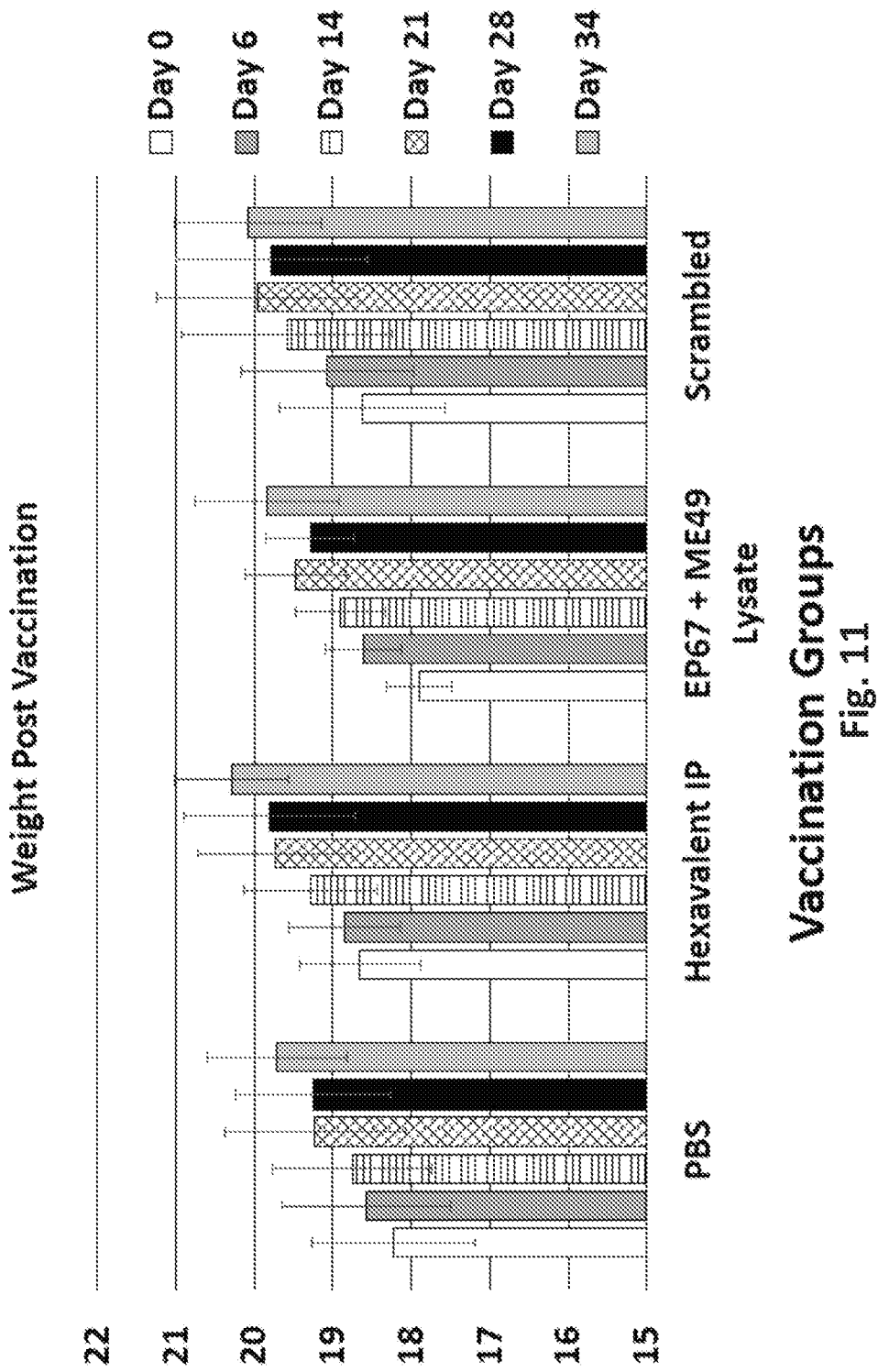
FIG. 11 shows recorded weights indicating a lack of toxicity in EP67-vaccinated mice.

Weight loss in mice is common signal of toxicity when exposed to foreign substances. EP67-containing vaccines would be ideal if no toxicity were observed during treatment. As seen in FIG. 11, no significant weight loss occurred following treatment of the mice (treated as outlined in FIG. 14). FIG. 11 shows recorded weights indicating a lack of toxicity in EP67-vaccinated mice. Mice administered all EP67-containing vaccines ("Hexavalent IP") at a total of 20 ug showed steady increases in weight, along with scrambled vaccine and PBS controls, in addition to EP67 mixed with parasite lysate. This is indicative of a lack of overt toxicity by EP67-containing vaccines in treated mice.

Figure 12:
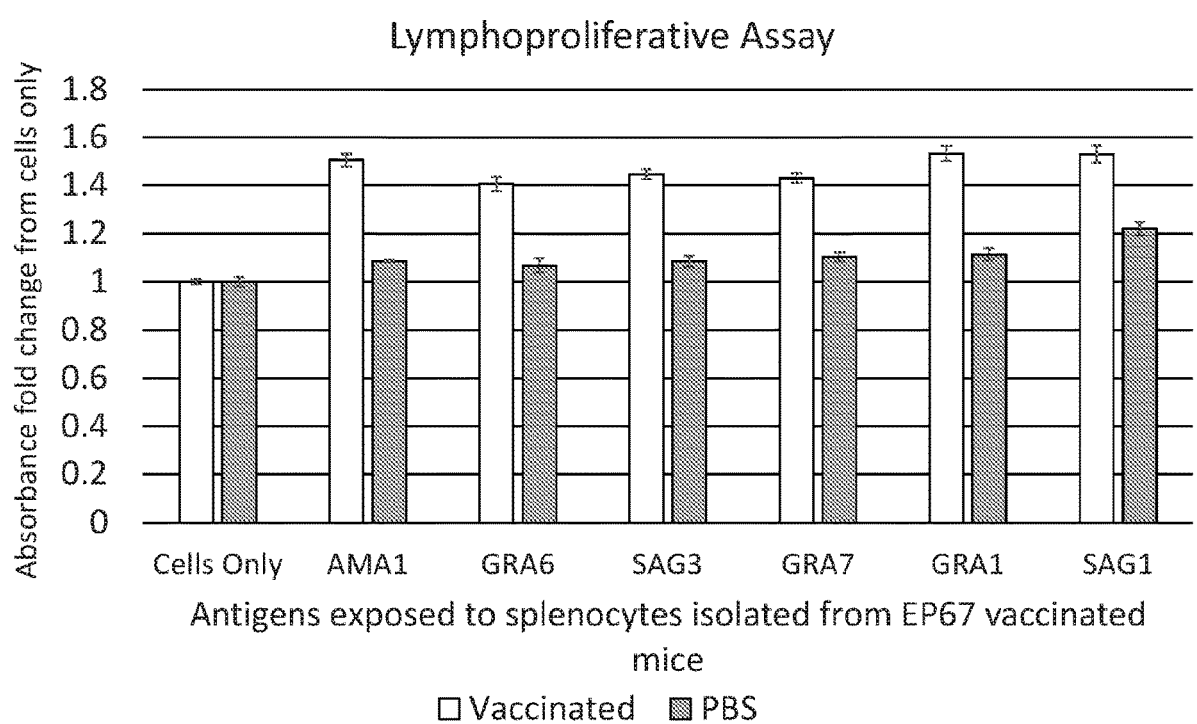
FIG. 12 shows results from the lymphoproliferative assay indicating specific antigen response.

Another criteria to be met which demonstrates antigen-specific immune activation is the splenic lymphoproliferative assay. FIG. 12 demonstrates that mice were specifically reactive to antigens when previously vaccinated with EP67-containing vaccines. FIG. 12 shows results from the lymphoproliferative assay indicating specific antigen response. Groups of mice (n=3) were vaccinated according to the scheme in FIG. 14. At day 45, mice were sacrificed and spleens removed. Following isolation, splenocytes were exposed for 72 hours to individual antigens (lacking EP67 moiety), then to MTT for 4 hours and quenched with DMSO. Absorbance was read at 540 nm, and relative increases in absorbance from unstimulated splenocytes were plotted. In ALL cases, antigens caused splenocytes proliferation in vaccinated mice, and not in PBS-treated mice. All p values<0.01 except SAG1, which is p=0.011 when evaluated by the Student's t test.

Example 10

EP67 Vaccines Activate Murine Macrophages

Figure 13A:
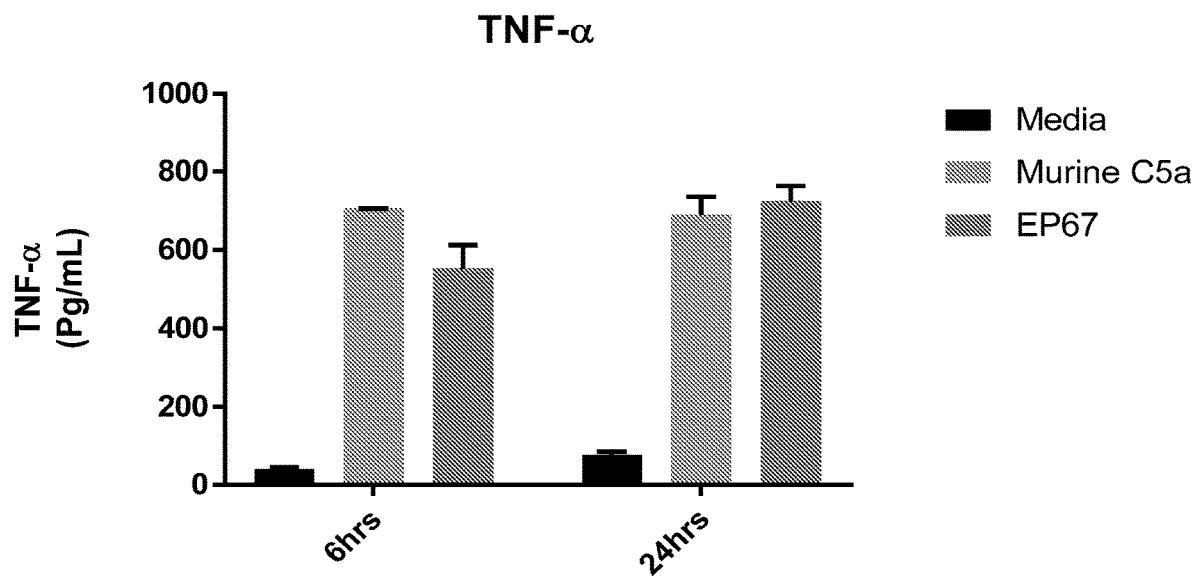
FIG. 13A shows secretion of TNF-α in RAW 264.7 cells exposed to recombinant C5a and EP67.
Figure 13B:
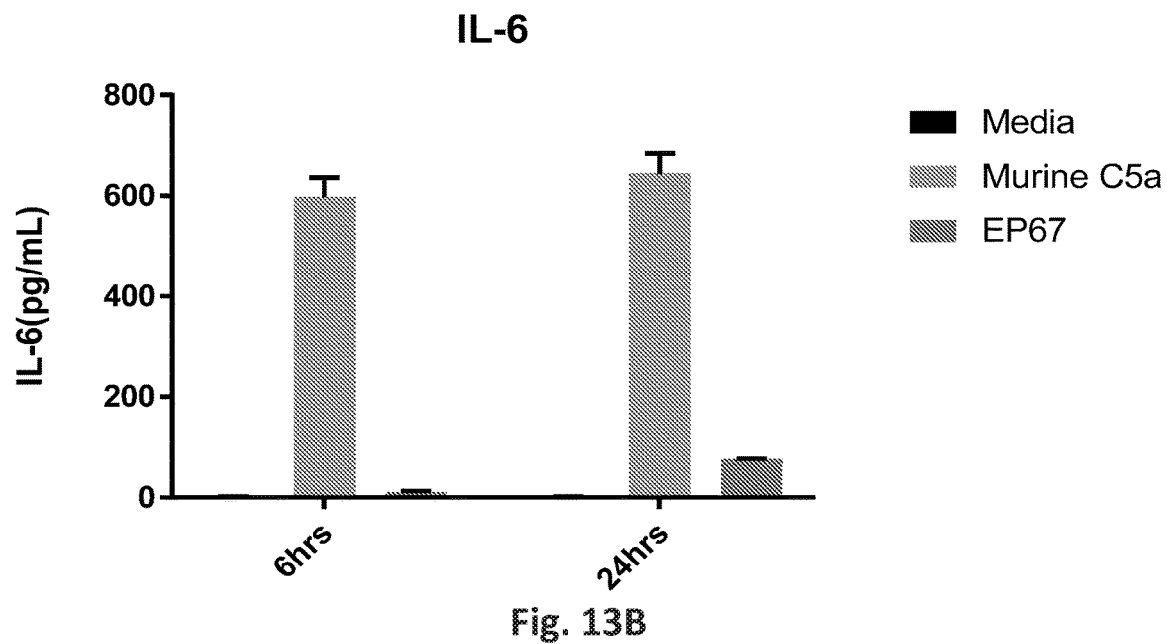
FIG. 13B shows secretion of IL-6 in RAW 264.7 cells exposed to recombinant C5a and EP67.

Although murine work was achieved using commercially available BALB/c cells, we felt it useful to explore additional cell options for in vitro evaluation of EP67 vaccine candidates. Using RAW 264.7 transformed cell lines, we were able to repeat the findings that EP67 does indeed activate this murine macrophage cell line, as measured by expression of TNF-alpha and IL-6 at levels significantly higher than media controls. FIGS. 13A and 13B show the results of RAW 264.7 cells activated by EP67. In order to evaluate a cell line that is responsive to both EP67 and C5a (the complement protein from which the sequence of EP67 is derived), RAW 264.7 were tested for secretion of TNF-a and IL-6. For both cytokines, supernatants from both 6 hr and 24 hr exposures of recombinant C5a were high. Additionally, EP67 caused statistically significant (p<0.05) increases in these two cytokines, with more pronounced effects at the later (24 hr) timepoint.

Example 11

EP67 Vaccine Confers Specific Immunity as Measured by IFN-Gamma Release

Figure 14:
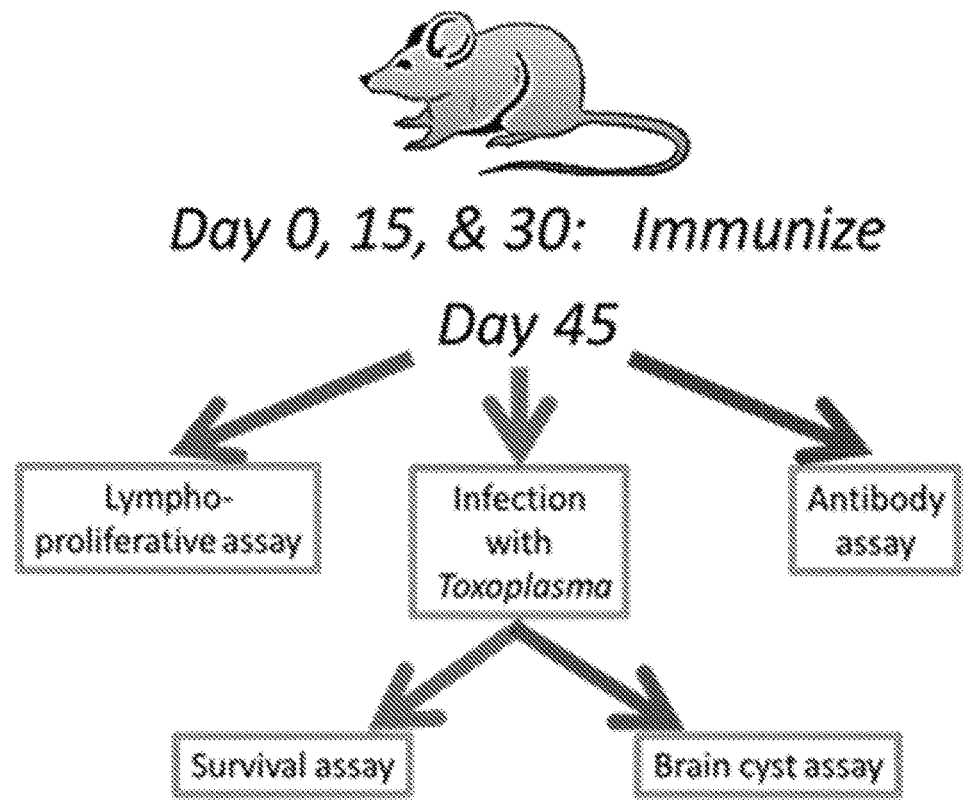
FIG. 14 illustrates the mouse vaccination schedule for FIGS. 11 and 12.
Figure 15:
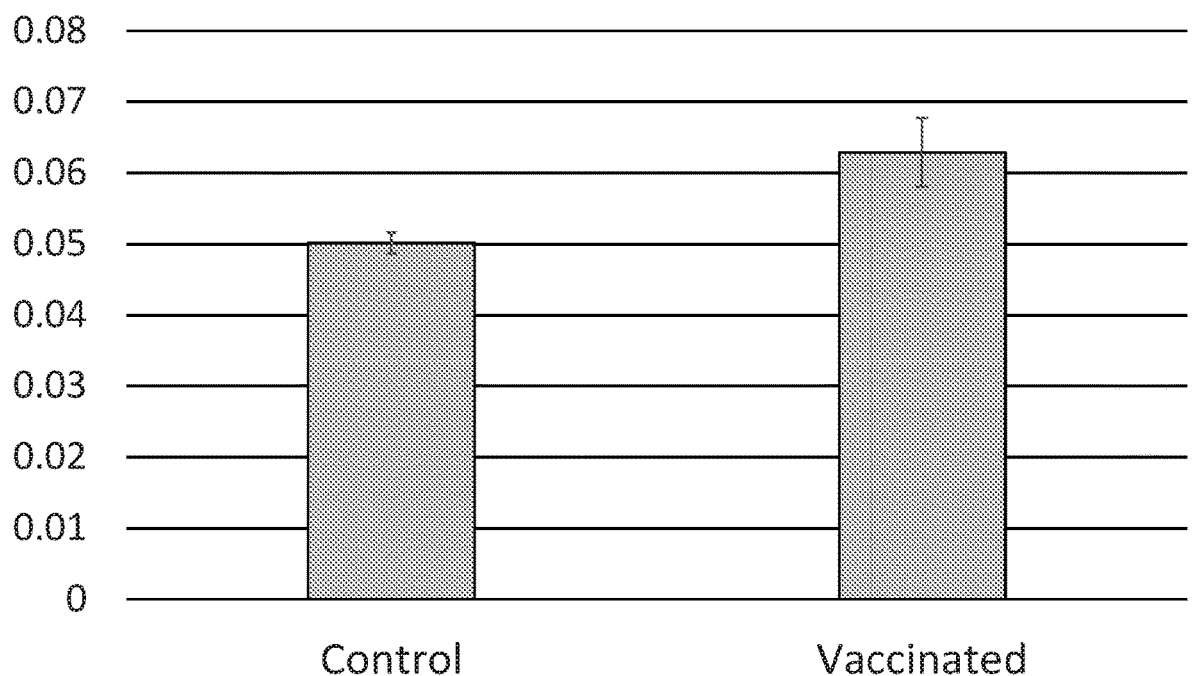
FIG. 15 is a graph of the Interferon Gamma ELISA results in the vaccinated mice models.
Figure 16:
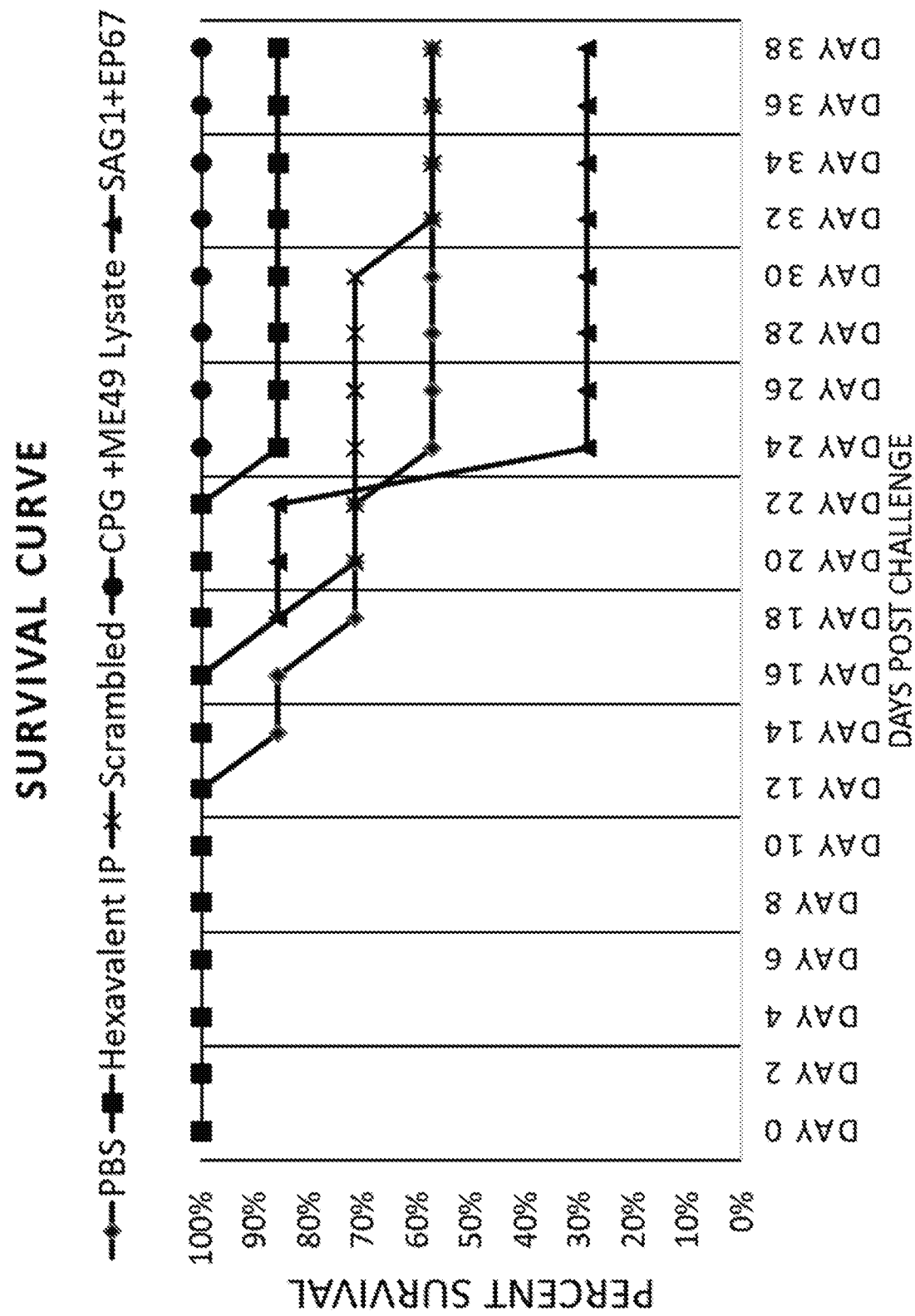
FIG. 16 is a graph of the survival curve for mice vaccinated and the challenged with *T. gondii* in the Examples.

Following the vaccination scheme outlined in FIG. 14, murine splenocytes were isolated from vaccinated and sham-vaccinated (control) mice. FIG. 15 demonstrates that the potent Th1-inducing interferon-gamma cytokine is released at significantly greater levels (p<0.01) when exposed to vaccinated antigen peptide vs splenocytes from control-treated mice. This indicates that EP67 vaccines can generate a specific, robust immune response against foreign peptides when vaccinated in this manner.

Example 12

Vaccination with EP67 Vaccines Prevented Mouse Death Following Acute Infection

Figure 17:
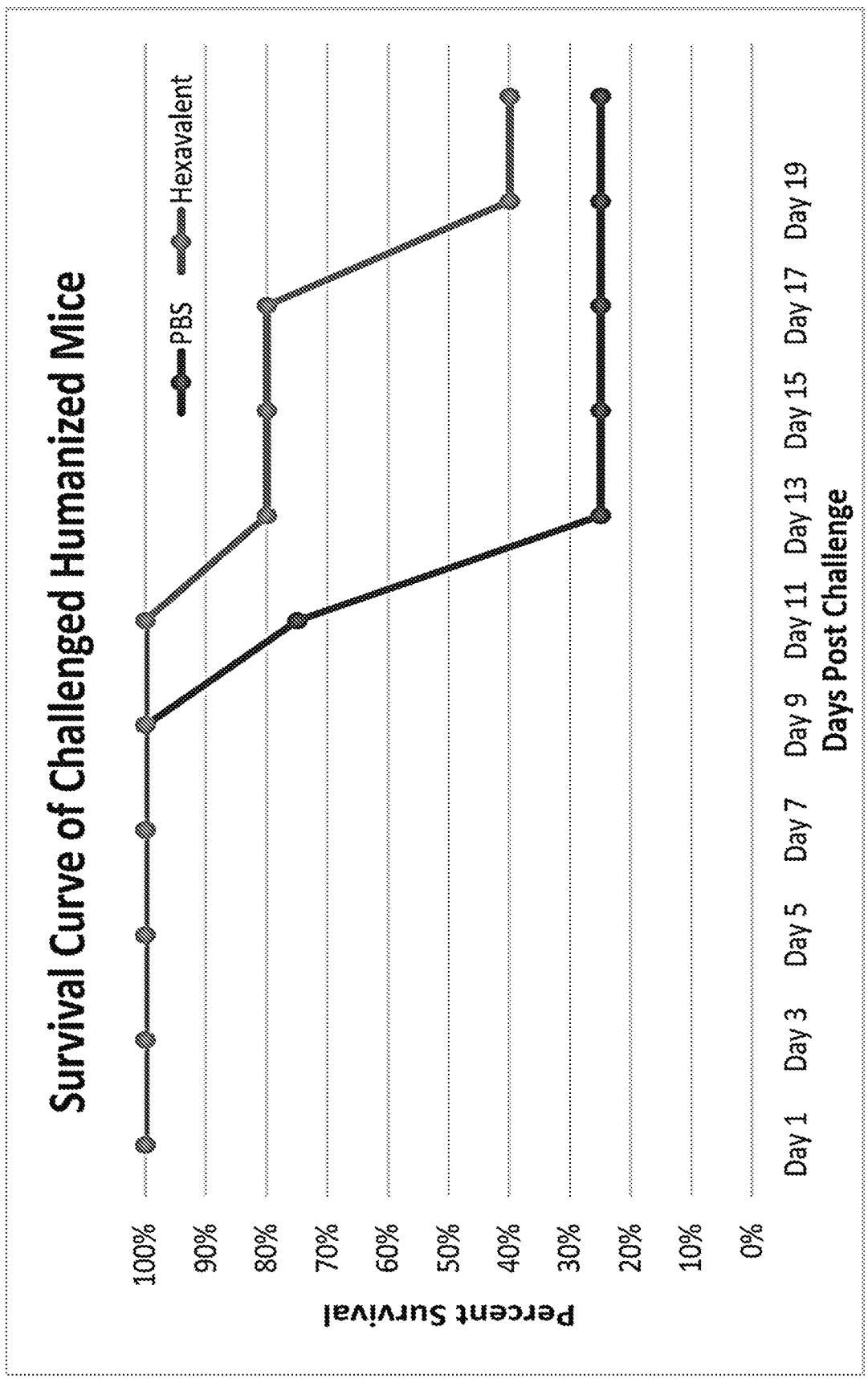
FIG. 17 is a graph demonstrating that the vaccine may prevent disease in humanized mice vaccinated in the Examples and challenged with *T. gondii*.
Figure 18:
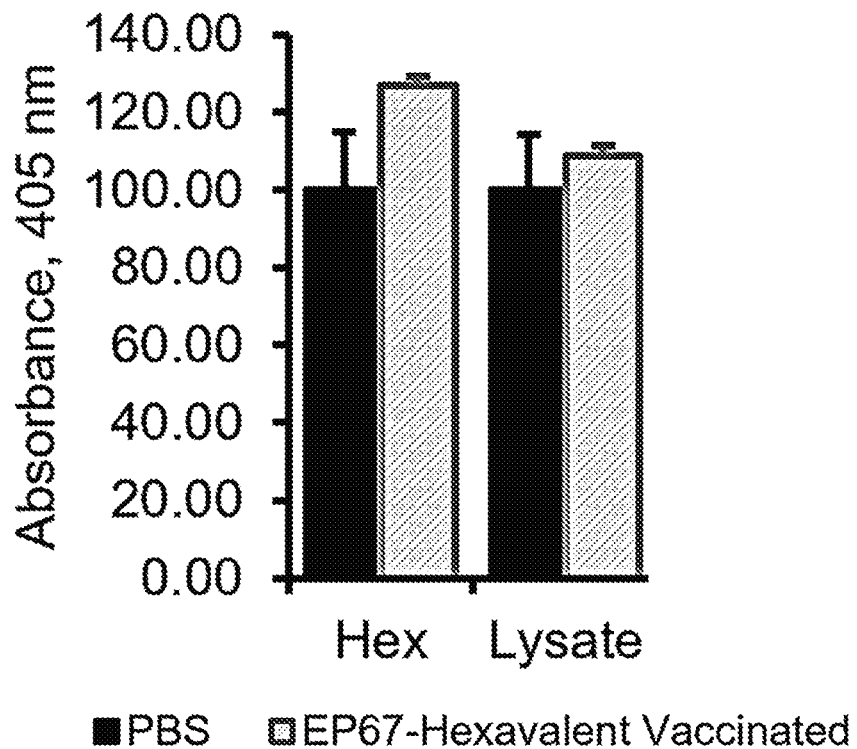
FIG. 18 is a graph of the results from the lymphoproliferative assay in the humanized mice vaccinated in the Examples.

Mice were infected with 5,000 ME49 *T. gondii* parasites intraperitoneally following 3 rounds of vaccine treatment. Non-vaccinated (PBS) mice (n=20) experienced incomplete lethality. A Student's t test of difference between PBS and Hexavalent EP67 vaccine intraperitoneal administration yielded a p-value of 0.08, indicating a strong likelihood of protection from EP67-containing vaccines. (FIG. 17) The recombinant parasite protein SAG1 co-administered with EP67 did not elicit any immune protection. As a positive control, ME49 parasite lysate was administered in conjunction with Th1-stimulating CpG DNA. FIG. 18 demonstrates an adaptive immune response in the vaccinated mice.

Example 13

Vaccine Prevented Parasite Encystment in Humanized Mice

Figure 19:
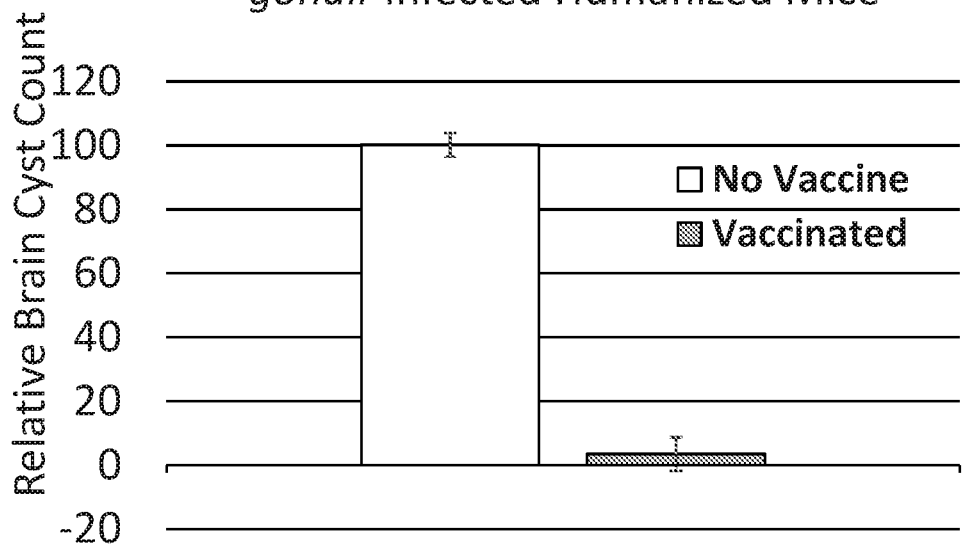
FIG. 19 is a graph of the brain cysts detected in mice vaccinated and the challenged with *T. gondii* in the Examples, showing a 28-fold decrease of cysts in 4 mice per group.

Humanized mice (containing a human MHC locus) received 4 vaccine administrations, or PBS as a No Vaccine control, and challenged 15 days with *T. gondii* following the final vaccination. 21 days post-infection, surviving mice were sacrificed and brains removed to ascertain brain parasite cyst loads via qPCR detection. Parasite cyst loads, relative to brain DNA in each sample, was calculated and showed at least a 28-fold decrease in cysts, with the potential for no cysts in the brain. A Students t test showed a p value of 0.01 between vaccinated and unvaccinated animals (FIG. 19). This data indicates that EP67 vaccines were able to substantially reduce brain tissue cysts in the brains of vaccinated and infected mice which contain elements of human adaptive immunity compared to sham-treated mice.

Conclusions

The anti-parasitic vaccines can generate specific splenic immune responses against 15mer antigens. The anti-parasitic vaccines can protect vaccinated mice against acute *T. gondii* infection w/ p-value=0.08. The anti-parasitic vaccines significantly reduce brain cysts w/ p-value<0.01.

Example 14

Treatment of Pigs for *T. gondii*

Figure 20:
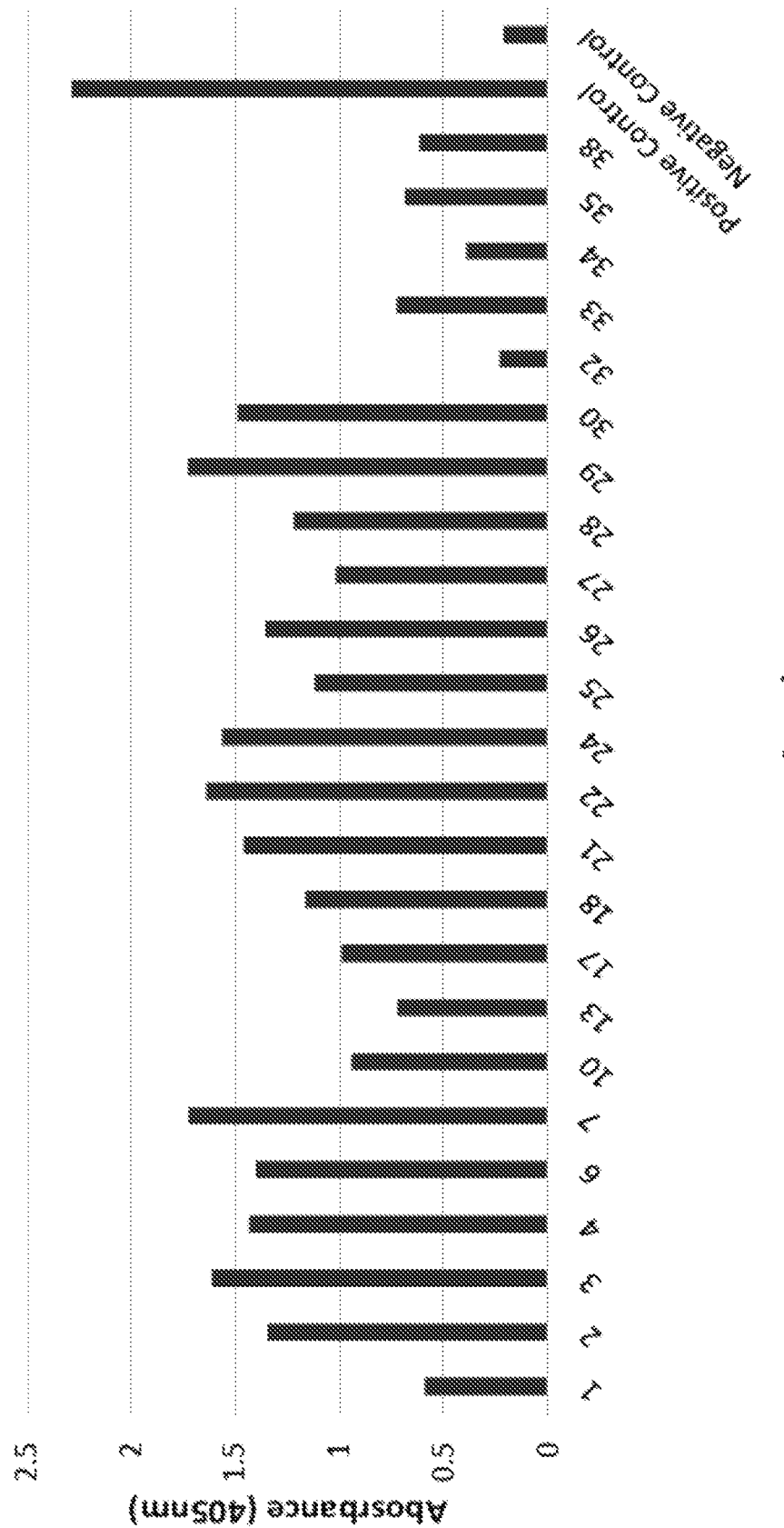
FIG. 20 is a graph of ELISA on serum collected from pigs, showing *T. gondii* infection.

The efficacy of the vaccines in generating an adaptive immune response as well as providing protection from chronic infection in pigs is investigated. Vaccines are prepared as described above. Vaccine sequences may be sequence optimized for pigs and synthesized accordingly. Pigs are first screened and identified as potential carriers of the parasite. Pig sera was received. ELISA plates coated with *T. gondii* soluble lysate were rinsed and soaked overnight with provided sera. After rinsing, goat anti-pig IgG labeled antibodies were added followed by a final rinse and HRP activation and absorbance reading. The sera were run in two separate replicate experiments, with identical results. Mouse positive and negative controls were used. Generally (in mice serology) an absorbance reading below 0.5 is considered negative. Between 0.5 and 1 is considered potentially positive. And above 1.0 is considered positive. As shown in FIG. 20, several of the pig sera contained IgG antibodies against *T. gondii*, although #32 and #34 would be considered negative.

Five separate groups of these pigs (10 pigs per group) will be immunized with:
1) Individual vaccines modeled on the ones identified in this application for mice but optimized for pigs using PigMatrix or other available swine MEW prediction tools
2) Pooled vaccines (2 or more vaccine combinations);
3) EP67-inactivated vaccines (scrambled or reversed orientation);
4) *T. gondii* epitopes only; and
5) Phosphate buffered saline (PBS) only.

Pigs screened and identified to have a high parasite burden (FIG. 20) will receive a total of up to 10 mg vaccine/peptide per dose in 3 doses every 15 days (e.g., days 0, 15, and 30). Each pig will be weighed and observed daily to identify any apparent toxicity. Two pigs from each group will be sacrificed and the spleen harvested to evaluate lymphoproliferative properties when mesh-purified and separately splenocytes are exposed to 50 µg/mL total parasite lysate (positively controlled by concanavalin A). Cell-free supernatants from this exposure will be probed via ELISA for secretion of IFN-gamma, considered vital in preventing *Toxoplasma*-induced acute disease following infection. Using collected sera, Western blots against total parasite lysate (or alternatively, purified recombinant protein) will confirm the target protein of the humoral response, and ELISA will quantitatively evaluate humoral response. The remaining pigs in each group will then be used for protection experiments (below).

It is anticipated that the pooled vaccine combination will produce the most significant TH1 adaptive immune responses as evidenced by these proposed experiments. As *Toxoplasma* relies primarily on its ability to rapidly disseminate in the host prior to adaptive immune activation, it is hypothesized that this EP67-adjuvanted approach using epitopes of *T. gondii* will be sufficient to prevent the deleterious effects of infection.

On Day 45, from the remaining pigs in each group, half will receive a sub-lethal dose of *T. gondii* strain ME49 tachyzoites designed to ensure the formation of brain cysts. All pigs will be maintained until Day 90.

It is anticipated that the prevention of brain cyst formation (chronic infection) will be granted to the EP67-containing vaccines (or pooled vaccines) that most potently elicits lymphoproliferative and humoral responses.

The invention claimed is:

1. A composition for inducing an immune response to *Toxoplasma gondii* infection, the composition comprising a plurality of peptides dispersed in a pharmaceutically acceptable carrier, said peptides each comprising an N-terminal peptide antigen conjugated to a C-terminal peptide adjuvant via a protease-cleavable linker, wherein said N-terminal peptide antigen is selected from the group consisting of SFKDILPKLSENPWQ (SEQ ID NO:19), EEVIDTMKSMQRDEE (SEQ ID NO:20), CAELCDPSNKPGHLL (SEQ ID NO:21), KRVTCGYPESGPVNL (SEQ ID NO:22), DRRPLHPGSVNEFDF (SEQ ID NO:23), and GLVAAALPQFATAAT (SEQ ID NO:24), and wherein said C-terminal peptide adjuvant is EP67 YSFKDMP(MeL)aR (SEQ ID NO:2), said plurality of peptides comprising at least two or more different peptides each having a different N-terminal peptide antigen.

2. The composition of claim 1, wherein said protease-cleavable linker comprises an arginine dipeptide.

3. A method for inducing an immune response to a parasitic infection caused by *Toxoplasma gondii*, said method comprising administering a composition according to claim 1 to a subject in need thereof.

4. The method of claim 3, further comprising providing a unit dosage form of said composition prior to said administering.

5. The composition of claim 1, wherein said peptides are HCl salt forms thereof.

6. The composition of claim 1, further comprising preservatives, buffering agents, salts, and mixtures thereof.

7. The composition of claim 1, said plurality of peptides comprising at least 3 or more different peptides each having a respective N-terminal peptide antigen that is different.

8. The composition of claim 1, said plurality of peptides comprising at least 4 or more different peptides each having a respective N-terminal peptide antigen that is different.

9. The composition of claim 1, said plurality of peptides comprising at least 5 or more different peptides each having a respective N-terminal peptide antigen that is different.

10. The composition of claim 1, wherein said peptides each comprise a sequence selected from the group consisting of: SFKDILPKLSENPWQ-RR-YSFKDMP(MeL)aR (SEQ ID NO:25), EEVIDTMKSMQRDEE-RR-YSFKDMP(MeL)aR (SEQ ID NO:26), CAELCDPSNKPGHLL-RR-YSFKDMP(MeL)aR (SEQ ID NO:27), KRVTCGYPESGPVNL-RR-YSFKDMP(MeL)aR (SEQ ID NO:28), DRRPLHPGSVNEFDF-RR-YSFKDMP(MeL)aR (SEQ ID NO:29), GLVAAALPQFATAAT-RR-YSFKDMP(MeL)aR (SEQ ID NO:30), and HCl salt forms thereof.

11. The composition of claim 1, said plurality of peptides comprising at least 6 different peptides each having a respective N-terminal peptide antigen that is different.

* * * * *

SEQUENCE LISTING

```
<160> NUMBER OF SEQ ID NOS: 78

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: Xaa is Ala, Leu, IsoLeu, Aib, 3ib, dmP, mbP,
      ebP, MeA, MeL, MeI, substituted Pro analog, pseudoproline, Ser- or
      Thr-derived oxazolidine, Cys-derived thiazolidine, Tfm azetidine,
      Tfm homoserine, oxetanyl, Aid, Nai, Agl, Aza, or pipecolic acid
<220> FEATURE:
<221> NAME/KEY: MOD_RES
<222> LOCATION: (8)..(8)
<223> OTHER INFORMATION: Xaa is Leu or N-methyl Leu
<220> FEATURE:
<221> NAME/KEY: MOD_RES
<222> LOCATION: (9)..(9)
<223> OTHER INFORMATION: D-Ala

<400> SEQUENCE: 1

Tyr Ser Phe Lys Asp Met Xaa Xaa Ala Arg
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: N-methyl Leu
<220> FEATURE:
<221> NAME/KEY: MOD_RES
```

```
<222> LOCATION: (9)..(9)
<223> OTHER INFORMATION: D-Ala

<400> SEQUENCE: 2

Tyr Ser Phe Lys Asp Met Pro Leu Ala Arg
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: Xaa is 2-aminoisobutyric acid
<220> FEATURE:
<221> NAME/KEY: MOD_RES
<222> LOCATION: (9)..(9)
<223> OTHER INFORMATION: D-Ala

<400> SEQUENCE: 3

Tyr Ser Phe Lys Asp Met Xaa Leu Ala Arg
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: Xaa is 5,5'-dimethylproline
<220> FEATURE:
<221> NAME/KEY: MOD_RES
<222> LOCATION: (8)..(8)
<223> OTHER INFORMATION: N-methyl Leu
<220> FEATURE:
<221> NAME/KEY: MOD_RES
<222> LOCATION: (9)..(9)
<223> OTHER INFORMATION: D-Ala

<400> SEQUENCE: 4

Tyr Ser Phe Lys Asp Met Xaa Leu Ala Arg
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is Tyr, Trp, or a N-acetyl derivatives of
      Tyr or Trp
<220> FEATURE:
<221> NAME/KEY: MOD_RES
<222> LOCATION: (5)..(5)
<223> OTHER INFORMATION: Xaa is Asp, Gly, Pro or a N-methyl derivatives
      of Asp or Gly
<220> FEATURE:
<221> NAME/KEY: MOD_RES
<222> LOCATION: (6)..(6)
<223> OTHER INFORMATION: Xaa is Ala, Cys, Leu, Met or a N-methyl
      derivatives of Ala, Cys, Leu or Met
<220> FEATURE:
<221> NAME/KEY: MOD_RES
<222> LOCATION: (7)..(7)
```

```
<223> OTHER INFORMATION: Xaa is Gln, Leu, Pro or a N-methyl derivatives
      of Gln or Leu
<220> FEATURE:
<221> NAME/KEY: MOD_RES
<222> LOCATION: (8)..(8)
<223> OTHER INFORMATION: Xaa is Pro, Leu, alpha-methyl Leu or N-methyl
      Leu
<220> FEATURE:
<221> NAME/KEY: MOD_RES
<222> LOCATION: (9)..(9)
<223> OTHER INFORMATION: Xaa is D-Ala, Gly, D-Pro, Aib or a N-methyl
      derivatives of D-Ala or Gly
<220> FEATURE:
<221> NAME/KEY: MOD_RES
<222> LOCATION: (10)..(10)
<223> OTHER INFORMATION: Xaa is Arg or N-methyl Arg

<400> SEQUENCE: 5

Xaa Ser Phe Lys Xaa Xaa Xaa Xaa Xaa Xaa
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: D-Ala

<400> SEQUENCE: 6

Tyr Ser Phe Lys Pro Met Pro Leu Ala Arg
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: D-Ala

<400> SEQUENCE: 7

Tyr Ser Phe Lys Asp Ala Pro Leu Ala Arg
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: D-Ala

<400> SEQUENCE: 8

Tyr Ser Phe Lys Asp Met Pro Leu Ala Arg
1               5                   10

<210> SEQ ID NO 9
<211> LENGTH: 10
<212> TYPE: PRT
<213> ORGANISM: Artificial Sequence
<220> FEATURE:
```

<223> OTHER INFORMATION: Synthetic peptide

<400> SEQUENCE: 9

Tyr Ser Phe Lys Asp Met Pro Leu Gly Arg
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic peptide

<400> SEQUENCE: 10

Tyr Ser Phe Lys Asp Ala Pro Leu Gly Arg
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic peptide

<400> SEQUENCE: 11

Tyr Ser Phe Lys Asp Cys Pro Leu Gly Arg
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: D-Pro

<400> SEQUENCE: 12

Tyr Ser Phe Lys Asp Met Pro Leu Pro Arg
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: D-Ala

<400> SEQUENCE: 13

Tyr Ser Phe Lys Asp Met Gln Leu Ala Arg
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide

<400> SEQUENCE: 14

Tyr Ser Phe Lys Asp Met Gln Leu Gly Arg
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic peptide

<400> SEQUENCE: 15

Tyr Ser Phe Lys Asp Met Gln Pro Gly Arg
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: Xaa is Aib

<400> SEQUENCE: 16

Tyr Ser Phe Lys Asp Met Pro Leu Xaa Arg
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic peptide

<400> SEQUENCE: 17

Tyr Ser Phe Lys Gly Met Pro Leu Gly Arg
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide

<400> SEQUENCE: 18

Tyr Ser Phe Lys Gly Leu Leu Leu Gly Arg
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

Ser Phe Lys Asp Ile Leu Pro Lys Leu Ser Glu Asn Pro Trp Gln
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic peptide

<400> SEQUENCE: 20

```
Glu Glu Val Ile Asp Thr Met Lys Ser Met Gln Arg Asp Glu Glu
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic peptide

<400> SEQUENCE: 21

Cys Ala Glu Leu Cys Asp Pro Ser Asn Lys Pro Gly His Leu Leu
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic peptide

<400> SEQUENCE: 22

Lys Arg Val Thr Cys Gly Tyr Pro Glu Ser Gly Pro Val Asn Leu
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic peptide

<400> SEQUENCE: 23

Asp Arg Arg Pro Leu His Pro Gly Ser Val Asn Glu Phe Asp Phe
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic peptide

<400> SEQUENCE: 24

Gly Leu Val Ala Ala Ala Leu Pro Gln Phe Ala Thr Ala Ala Thr
1               5                   10                  15

<210> SEQ ID NO 25
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (25)..(25)
<223> OTHER INFORMATION: N-methyl Leu
<220> FEATURE:
<221> NAME/KEY: MOD_RES
<222> LOCATION: (26)..(26)
<223> OTHER INFORMATION: D-Ala

<400> SEQUENCE: 25

Ser Phe Lys Asp Ile Leu Pro Lys Leu Ser Glu Asn Pro Trp Gln Arg
1               5                   10                  15

Arg Tyr Ser Phe Lys Asp Met Pro Leu Ala Arg
            20                  25
```

<210> SEQ ID NO 26
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (25)..(25)
<223> OTHER INFORMATION: N-methyl Leu
<220> FEATURE:
<221> NAME/KEY: MOD_RES
<222> LOCATION: (26)..(26)
<223> OTHER INFORMATION: D-Ala

<400> SEQUENCE: 26

Glu Glu Val Ile Asp Thr Met Lys Ser Met Gln Arg Asp Glu Arg
1               5                   10                  15

Arg Tyr Ser Phe Lys Asp Met Pro Leu Ala Arg
            20                  25

<210> SEQ ID NO 27
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (25)..(25)
<223> OTHER INFORMATION: N-methyl Leu
<220> FEATURE:
<221> NAME/KEY: MOD_RES
<222> LOCATION: (26)..(26)
<223> OTHER INFORMATION: D-Ala

<400> SEQUENCE: 27

Cys Ala Glu Leu Cys Asp Pro Ser Asn Lys Pro Gly His Leu Leu Arg
1               5                   10                  15

Arg Tyr Ser Phe Lys Asp Met Pro Leu Ala Arg
            20                  25

<210> SEQ ID NO 28
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (25)..(25)
<223> OTHER INFORMATION: N-methyl Leu
<220> FEATURE:
<221> NAME/KEY: MOD_RES
<222> LOCATION: (26)..(26)
<223> OTHER INFORMATION: D-Ala

<400> SEQUENCE: 28

Lys Arg Val Thr Cys Gly Tyr Pro Glu Ser Gly Pro Val Asn Leu Arg
1               5                   10                  15

Arg Tyr Ser Phe Lys Asp Met Pro Leu Ala Arg
            20                  25

<210> SEQ ID NO 29
<211> LENGTH: 27
<212> TYPE: PRT
<213> ORGANISM: Artificial Sequence
<220> FEATURE:

```
<223> OTHER INFORMATION: Synthetic peptide
<220> FEATURE:
<221> NAME/KEY: MOD_RES
<222> LOCATION: (25)..(25)
<223> OTHER INFORMATION: N-methyl Leu
<220> FEATURE:
<221> NAME/KEY: MOD_RES
<222> LOCATION: (26)..(26)
<223> OTHER INFORMATION: D-Ala

<400> SEQUENCE: 29

Asp Arg Arg Pro Leu His Pro Gly Ser Val Asn Glu Phe Asp Phe Arg
1               5                   10                  15

Arg Tyr Ser Phe Lys Asp Met Pro Leu Ala Arg
            20                  25

<210> SEQ ID NO 30
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (25)..(25)
<223> OTHER INFORMATION: N-methyl Leu
<220> FEATURE:
<221> NAME/KEY: MOD_RES
<222> LOCATION: (26)..(26)
<223> OTHER INFORMATION: D-Ala

<400> SEQUENCE: 30

Gly Leu Val Ala Ala Ala Leu Pro Gln Phe Ala Thr Ala Ala Thr Arg
1               5                   10                  15

Arg Tyr Ser Phe Lys Asp Met Pro Leu Ala Arg
            20                  25

<210> SEQ ID NO 31
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: N-methyl Leu
<220> FEATURE:
<221> NAME/KEY: MOD_RES
<222> LOCATION: (24)..(24)
<223> OTHER INFORMATION: D-Ala

<400> SEQUENCE: 31

Ser Phe Lys Asp Ile Leu Pro Lys Leu Ser Glu Asn Pro Trp Gln Arg
1               5                   10                  15

Arg Leu Arg Met Tyr Lys Pro Ala Phe Asp Ser
            20                  25

<210> SEQ ID NO 32
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: N-methyl Leu
<220> FEATURE:
<221> NAME/KEY: MOD_RES
```

```
<222> LOCATION: (24)..(24)
<223> OTHER INFORMATION: D-Ala

<400> SEQUENCE: 32

Glu Glu Val Ile Asp Thr Met Lys Ser Met Gln Arg Asp Glu Glu Arg
1               5                   10                  15

Arg Leu Arg Met Tyr Lys Pro Ala Phe Asp Ser
            20                  25

<210> SEQ ID NO 33
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: N-methyl Leu
<220> FEATURE:
<221> NAME/KEY: MOD_RES
<222> LOCATION: (24)..(24)
<223> OTHER INFORMATION: D-Ala

<400> SEQUENCE: 33

Cys Ala Glu Leu Cys Asp Pro Ser Asn Lys Pro Gly His Leu Leu Arg
1               5                   10                  15

Arg Leu Arg Met Tyr Lys Pro Ala Phe Asp Ser
            20                  25

<210> SEQ ID NO 34
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: N-methyl Leu
<220> FEATURE:
<221> NAME/KEY: MOD_RES
<222> LOCATION: (24)..(24)
<223> OTHER INFORMATION: D-Ala

<400> SEQUENCE: 34

Lys Arg Val Thr Cys Gly Tyr Pro Glu Ser Gly Pro Val Asn Leu Arg
1               5                   10                  15

Arg Leu Arg Met Tyr Lys Pro Ala Phe Asp Ser
            20                  25

<210> SEQ ID NO 35
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: N-methyl Leu
<220> FEATURE:
<221> NAME/KEY: MOD_RES
<222> LOCATION: (24)..(24)
<223> OTHER INFORMATION: D-Ala

<400> SEQUENCE: 35

Asp Arg Arg Pro Leu His Pro Gly Ser Val Asn Glu Phe Asp Phe Arg
1               5                   10                  15
```

Arg Leu Arg Met Tyr Lys Pro Ala Phe Asp Ser
            20                  25

<210> SEQ ID NO 36
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: N-methyl Leu
<220> FEATURE:
<221> NAME/KEY: MOD_RES
<222> LOCATION: (24)..(24)
<223> OTHER INFORMATION: D-Ala

<400> SEQUENCE: 36

Gly Leu Val Ala Ala Ala Leu Pro Gln Phe Ala Thr Ala Ala Thr Arg
1               5                   10                  15
Arg Leu Arg Met Tyr Lys Pro Ala Phe Asp Ser
            20                  25

<210> SEQ ID NO 37
<211> LENGTH: 9
<212> TYPE: PRT
<213> ORGANISM: Artificial Sequence
<220> FEATURE:
<223> OTHER INFORMATION: Synthetic peptide

<400> SEQUENCE: 37

Val Val Phe Val Val Phe Met Gly Val
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic peptide

<400> SEQUENCE: 38

Phe Met Gly Val Leu Val Asn Ser Leu
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic peptide

<400> SEQUENCE: 39

Phe Leu Val Pro Phe Val Val Phe Leu
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic peptide

<400> SEQUENCE: 40

Lys Ser Phe Lys Asp Ile Leu Pro Lys
1               5

```
<210> SEQ ID NO 41
<211> LENGTH: 9
<212> TYPE: PRT
<213> ORGANISM: Artificial Sequence
<220> FEATURE:
<223> OTHER INFORMATION: Synthetic peptide

<400> SEQUENCE: 41

Ala Met Leu Thr Ala Phe Phe Leu Arg
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic peptide

<400> SEQUENCE: 42

Arg Ser Phe Lys Asp Leu Leu Lys Lys
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide

<400> SEQUENCE: 43

Leu Pro Gln Phe Ala Thr Ala Ala Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide

<400> SEQUENCE: 44

Val Pro Phe Val Val Phe Leu Val Ala
1               5

<210> SEQ ID NO 45
<211> LENGTH: 10
<212> TYPE: PRT
<213> ORGANISM: Artificial Sequence
<220> FEATURE:
<223> OTHER INFORMATION: Synthetic peptide

<400> SEQUENCE: 45

His Pro Gly Ser Val Asn Glu Phe Asp Phe
1               5                   10

<210> SEQ ID NO 46
<211> LENGTH: 9
<212> TYPE: PRT
<213> ORGANISM: Artificial Sequence
<220> FEATURE:
<223> OTHER INFORMATION: Synthetic peptide

<400> SEQUENCE: 46

Ser Thr Phe Trp Pro Cys Leu Leu Arg
1               5
```

```
<210> SEQ ID NO 47
<211> LENGTH: 10
<212> TYPE: PRT
<213> ORGANISM: Artificial Sequence
<220> FEATURE:
<223> OTHER INFORMATION: Synthetic peptide

<400> SEQUENCE: 47

Ala Val Val Ser Leu Leu Arg Leu Leu Lys
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Synthetic peptide

<400> SEQUENCE: 48

Ser Ser Ala Tyr Val Phe Ser Val Lys
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic peptide

<400> SEQUENCE: 49

Leu Leu Ala Val Cys Met Ser Gly Val
1               5

<210> SEQ ID NO 50
<211> LENGTH: 10
<212> TYPE: PRT
<213> ORGANISM: Artificial Sequence
<220> FEATURE:
<223> OTHER INFORMATION: Synthetic peptide

<400> SEQUENCE: 50

Phe Asn Met Asn Phe Tyr Ile Ile Gly Ala
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic peptide

<400> SEQUENCE: 51

Tyr Leu Gly Tyr Cys Ala Leu Leu Pro Leu
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Synthetic peptide

<400> SEQUENCE: 52

Lys Leu Met Arg Gln Tyr Asp Met Met Val
1               5                   10
```

<210> SEQ ID NO 53
<211> LENGTH: 9
<212> TYPE: PRT
<213> ORGANISM: Artificial Sequence
<220> FEATURE:
<223> OTHER INFORMATION: Synthetic peptide

<400> SEQUENCE: 53

Arg Leu Gln Glu Ile Ile Ala Leu Ala
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic peptide

<400> SEQUENCE: 54

Phe Leu Ala Gly Ser Gln Val Pro Gly
1               5

<210> SEQ ID NO 55
<211> LENGTH: 10
<212> TYPE: PRT
<213> ORGANISM: Artificial Sequence
<220> FEATURE:
<223> OTHER INFORMATION: Synthetic peptide

<400> SEQUENCE: 55

Phe Met Ile Ala Phe Ile Ser Cys Phe Ala
1               5                   10

<210> SEQ ID NO 56
<211> LENGTH: 9
<212> TYPE: PRT
<213> ORGANISM: Artificial Sequence
<220> FEATURE:
<223> OTHER INFORMATION: Synthetic peptide

<400> SEQUENCE: 56

Phe Leu Ser Leu Ser Leu Leu Val Ile
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic peptide

<400> SEQUENCE: 57

Ser Leu Pro Leu Ser Pro Phe Thr Val
1               5

<210> SEQ ID NO 58
<211> LENGTH: 10
<212> TYPE: PRT
<213> ORGANISM: Artificial Sequence
<220> FEATURE:
<223> OTHER INFORMATION: Synthetic peptide

<400> SEQUENCE: 58

Phe Met Ile Ala Phe Ile Ser Cys Phe Ala
1               5                   10

<210> SEQ ID NO 59

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 59

Phe Met Ile Val Ser Ile Ser Leu Val
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic peptide

<400> SEQUENCE: 60

Val Leu Ser Ser Ser Phe Met Ile Val
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic peptide

<400> SEQUENCE: 61

Phe Val Ile Phe Ala Cys Asn Phe Val
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic peptide

<400> SEQUENCE: 62

Cys Leu Pro Leu Tyr Leu Phe Val Ile
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic peptide

<400> SEQUENCE: 63

Phe Leu Leu Gly Leu Leu Val His Val
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic peptide

<400> SEQUENCE: 64

Phe Leu Thr Asp Tyr Ile Pro Gly Ala
1               5

<210> SEQ ID NO 65
<211> LENGTH: 9
```

```
<212> TYPE: PRT
<213> ORGANISM: Artificial Sequence
<220> FEATURE:
<223> OTHER INFORMATION: Synthetic peptide

<400> SEQUENCE: 65

Phe Leu Val Gly Cys Ser Leu Thr Val
1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic peptide

<400> SEQUENCE: 66

Val Ser Gly Phe Val Val Ala Ser
1               5

<210> SEQ ID NO 67
<211> LENGTH: 10
<212> TYPE: PRT
<213> ORGANISM: Artificial Sequence
<220> FEATURE:
<223> OTHER INFORMATION: Synthetic peptide

<400> SEQUENCE: 67

Lys Leu Met Ala Val Cys Ile Gly Gly Ile
1               5                   10

<210> SEQ ID NO 68
<211> LENGTH: 9
<212> TYPE: PRT
<213> ORGANISM: Artificial Sequence
<220> FEATURE:
<223> OTHER INFORMATION: Synthetic peptide

<400> SEQUENCE: 68

Ile Thr Met Gly Ser Leu Phe Phe Val
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic peptide

<400> SEQUENCE: 69

Lys Leu Ala Asp Val Leu Pro Ser Ala
1               5

<210> SEQ ID NO 70
<211> LENGTH: 10
<212> TYPE: PRT
<213> ORGANISM: Artificial Sequence
<220> FEATURE:
<223> OTHER INFORMATION: Synthetic peptide

<400> SEQUENCE: 70

Phe Leu Cys Asp Met Asp Ile Ala Thr Leu
1               5                   10

<210> SEQ ID NO 71
<211> LENGTH: 9
<212> TYPE: PRT
```

```
<213> ORGANISM: Artificial Sequence
<220> FEATURE:
<223> OTHER INFORMATION: Synthetic peptide

<400> SEQUENCE: 71

Val Leu Ala Leu Ile Phe Val Gly Val
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic peptide

<400> SEQUENCE: 72

Gly Leu Ala Ala Ala Val Val Ala Val
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic peptide

<400> SEQUENCE: 73

Val Leu Leu Pro Val Leu Phe Gly Val
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic peptide

<400> SEQUENCE: 74

Tyr Leu Ile Gly Ser Gly Phe Ser Ala
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic peptide

<400> SEQUENCE: 75

Met Met Pro Ser Gly Val Pro Met Ala
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic peptide

<400> SEQUENCE: 76

Phe Ala Ala Ala Phe Phe Pro Ala Val
1               5

<210> SEQ ID NO 77
<211> LENGTH: 10
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-methyl Leu
<220> FEATURE:
<221> NAME/KEY: MOD_RES
<222> LOCATION: (7)..(7)
<223> OTHER INFORMATION: D-Ala

<400> SEQUENCE: 77

Leu Arg Met Tyr Lys Pro Ala Phe Asp Ser
1               5                   10

<210> SEQ ID NO 78
<211> LENGTH: 4
<212> TYPE: PRT
<213> ORGANISM: Artificial Sequence
<220> FEATURE:
<223> OTHER INFORMATION: Synthetic peptide

<400> SEQUENCE: 78

Arg Val Arg Arg
1
```